United States Patent
Cheng et al.

(10) Patent No.: US 6,309,353 B1
(45) Date of Patent: Oct. 30, 2001

(54) METHODS AND APPARATUS FOR TUMOR DIAGNOSIS

(75) Inventors: Xiangyong Cheng, Ishikawa; Iwaki Akiyama, Kanagawa; Kouichi Itoh, Tochigi, all of (JP)

(73) Assignee: Mitani Sangyo Co., Ltd., Ishikawa (JP)

( * ) Notice: Subject to any disclaimer, the term of this patent is extended or adjusted under 35 U.S.C. 154(b) by 0 days.

(21) Appl. No.: 09/246,727

(22) Filed: Feb. 9, 1999

(30) Foreign Application Priority Data

Oct. 27, 1998 (JP) .................................................. 10-305420

(51) Int. Cl.[7] .......................................................... A61B 8/01
(52) U.S. Cl. ............................................. 600/437; 600/443
(58) Field of Search ................................... 600/443, 447, 600/446, 437, 444

(56) References Cited

U.S. PATENT DOCUMENTS 5,876,343 * 3/1999 Chen et al. ........................... 600/443
6,132,376 * 10/2000 Hossack et al. ..................... 600/443

FOREIGN PATENT DOCUMENTS 5-123318    5/1993  (JP) .

* cited by examiner

Primary Examiner—Marvin M. Lateef
Assistant Examiner—Maulin Patel
(74) Attorney, Agent, or Firm—McDermott, Will & Emery

(57) ABSTRACT

Method and apparatus for extraction of breast tumors from three-dimensional ultrasonic images obtained by interpolation of a series of cross sectional images. The method consists of two stages are disclosed. In the first stage a membership function is automatically generated by using an output of three dimensional LoG(Laplace of Gaussian) filtering for the voxel data. In the second stage, the membership function is used for a fuzzy logic based calculation to produce three grades of the voxel attributable to three classes of "tumor", "normal tissue" and "boundary". We then classify each voxel as one of the three classes by relaxation techniques. Also, a parameter for evaluation of the uneven complexity of the surface roughness using a ratio of the surface area over the volume is defined.

6 Claims, 17 Drawing Sheets

FIG. 20
| CASES | AGE | SIZE [cm] | PATHOLOGY |
|---|---|---|---|
| (1) | 77 | 1.2 | MALIGNANT |
| (2) | 76 | 0.9 | MALIGNANT |
| (3) | 42 | 1.2 | MALIGNANT |
| (4) | 32 | 1.5 | MALIGNANT |
| (5) | 44 | 0.8 | MALIGNANT |
| (6) | 65 | 1.5 | MALIGNANT |
| (7) | 61 | 1.0 | MALIGNANT |
| (8) | 70 | 1.1 | MALIGNANT |
| (9) | 52 | 1.7 | MALIGNANT |
| (10) | 70 | 1.1 | MALIGNANT |
| (11) | 65 | 1.0 | MALIGNANT |
| (12) | 74 | 1.8 | MALIGNANT |
| (13) | 49 | 1.0 | MALIGNANT |
| (14) | 51 | 1.2 | MALIGNANT |
| (15) | 45 | 1.5 | MALIGNANT |
| (16) | 59 | 1.6 | MALIGNANT |
| (17) | 49 | 0.7 | BENIGN |
| (18) | 42 | 0.8 | BENIGN |
| (19) | 49 | 0.5 | BENIGN |
| (20) | 35 | 0.7 | BENIGN |
| (21) | 27 | 0.6 | BENIGN |
| (22) | 44 | 1.0 | BENIGN |
| (23) | 56 | 1.3 | BENIGN |
| (24) | 49 | 1.2 | BENIGN |
| (25) | 35 | 0.9 | BENIGN |
| (26) | 25 | 0.7 | BENIGN |
| (27) | 43 | 0.9 | BENIGN |
FIG. 21A
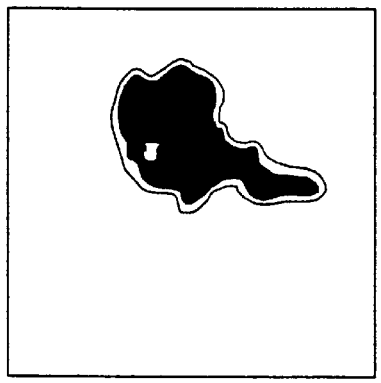
FIG. 21B
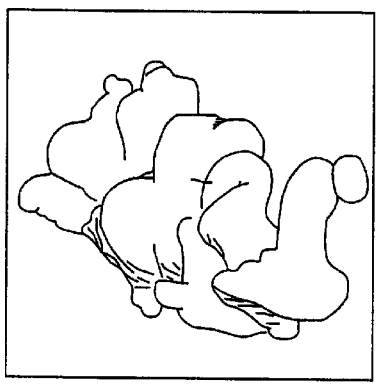

FIG. 30A
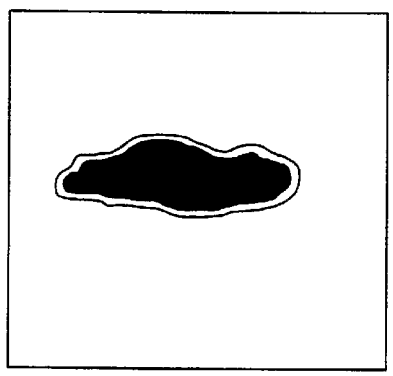
FIG. 30B
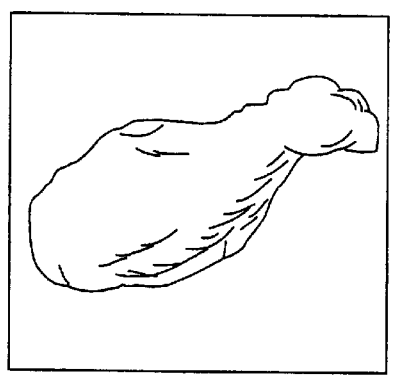
FIG. 31
| CASES | AGE | VOL.[cm³] | γ | PATHOLOGY |
|---|---|---|---|---|
| (1) | 77 | 0.35 | 7.78 | MALIGNANT |
| (2) | 76 | 0.25 | 6.88 | MALIGNANT |
| (3) | 42 | 0.28 | 4.92 | MALIGNANT |
| (4) | 32 | 0.38 | 9.43 | MALIGNANT |
| (5) | 44 | 0.21 | 7.89 | MALIGNANT |
| (6) | 65 | 0.66 | 12.8 | MALIGNANT |
| (7) | 61 | 0.37 | 8.79 | MALIGNANT |
| (8) | 70 | 0.21 | 4.36 | MALIGNANT |
| (9) | 52 | 1.27 | 5.34 | MALIGNANT |
| (10) | 70 | 0.38 | 13.1 | MALIGNANT |
| (11) | 65 | 0.28 | 10.6 | MALIGNANT |
| (12) | 74 | 0.45 | 9.35 | MALIGNANT |
| (13) | 49 | 0.33 | 8.98 | MALIGNANT |
| (14) | 51 | 0.29 | 9.25 | MALIGNANT |
| (15) | 45 | 0.51 | 7.14 | MALIGNANT |
| (16) | 59 | 0.56 | 4.59 | MALIGNANT |
| (17) | 49 | 0.11 | 3.13 | BENIGN |
| (18) | 42 | 0.13 | 3.29 | BENIGN |
| (19) | 49 | 0.06 | 1.42 | BENIGN |
| (20) | 35 | 0.08 | 1.89 | BENIGN |
| (21) | 27 | 0.07 | 3.27 | BENIGN |
| (22) | 44 | 0.47 | 3.89 | BENIGN |
| (23) | 56 | 0.56 | 1.48 | BENIGN |
| (24) | 49 | 0.13 | 2.95 | BENIGN |
| (25) | 35 | 0.17 | 3.06 | BENIGN |
| (26) | 25 | 0.12 | 2.68 | BENIGN |
| (27) | 43 | 0.15 | 3.06 | BENIGN |

METHODS AND APPARATUS FOR TUMOR DIAGNOSIS

FIELD OF THE INVENTION

The present invention relates to methods and apparatus for tumor diagnosis by measuring and evaluating morphological surface roughness of tumor which is drawn in detail as a three dimensional image.

More specifically, present invention relates to methods and apparatus for tumor diagnosis that can be applied to pathological diagnosis support system, which discovers cancer tissue (especially breast cancer tissue) among normal tissue by extracting boundary between the cancer tissue and the normal tissue from three dimensional image made from two dimensional cross sectional image such as magnetic resonance image or ultrasonic echography image.

BACKGROUND OF THE INVENTION

Breast cancer is a major cause of death among women over the age of forty. It is significant to discriminate and specify the malignant tumors among the various tumors. Prevention and early diagnosis of breast cancer are of foremost importance. Since there are various kinds of tumors in the mammary gland, it is significant to discriminate and specify the malignant tumors among the various tumors.

X-ray mammography and ultrasonic echography are mostly used for diagnosis of the breast tumors. Mammography is an X-ray transmission imaging technique. This technique has been studied proposed by C. Kimme and D. Wei, and known as local texture analysis. Or binary digitizes method proposed by D. Brzakovic. Alternatively, an ultrasonic echography is a cross sectional imaging based on pulse-echo technique. A characteristic of malignant tumors is that the tumor boundaries appear as uneven complex shapes.

This geometrical characteristic is usually evident in the image diagnosis. So far, several approaches have been proposed for detection and evaluation of malignant tumors in the mammography.

On the other hand, the diagnosis of breast tumors using echography has an advantage over early detection of the malignant tumors, because there is capability to produce a three dimensional image of the tumor from a series of cross sectional images, and thus there is a potential to evaluate the surface roughness of a tumor in three dimensional space. This kind of method is opened, for example, in Japanese Patent Laid-open Publication No.93-123318.

The ultrasonic images, however, are degraded by speckle noise and various kinds of artifacts due to reflection, refraction, and so on, thus the conventional image processing is not applicable for the automated extraction of tumors. Consequently, well-experienced inspector can observe cross sectional image of inner of mammary gland on screen with scanning the probe on the body over the mammary gland. And tumors can be discovered and malignant tumor can be distinguished with high accuracy from benign tumor by the inspector. Although, herein a problem arises. To achieve precise (or reliable) diagnosis, it depends on the experience of the inspector, because of the fact that a set of cross sectional images (or views onscreen) requires experience to analyze and diagnose the tumor precisely. And it is difficult to grasp the information about real morphological surface roughness and 3D-shape from the cross sectional 2D-images. The object of interest other than breast tumor is, for example, heart or bladder of embryo. In such a diagnostic for cardiovascular disease, the original image data necessary to construct the third dimensional Figure, which change on the time axis, are multislice Figure of whole heart containing plural phase in one pulsation.

As Figure information on border Figure of heart and inner space of blood vessels or extima and other space also as the third dimensional (3D) distribution of blood flow in the heart and blood vessels.

Also in the application described above, it is significant for achieving the precise and reliable diagnosis to obtain a 3D(three-dimensional) image.

SUMMARY OF THE INVENTION

Present invention features methods and apparatus for tumor diagnosis (or, in other words, tumor diagnosis system) using three-dimensional ultrasonic echographic images. Since a malignant tumor is characterized by the morphological surface roughness, it is significant for the diagnosis to extract the exact boundaries of the tumor and show the three dimensional structure of the tumors. The proposed system consists of three-dimensional image capturing system and a fuzzy reasoning based algorithm for the extraction of breast tumors. The method we proposed in this paper classifies all the voxel as one of "tumor", "normal tissue", or "boundary" by employing fuzzy reasoning and relaxation techniques. In order to evaluate the surface roughness, we define a parameter of a ratio of the surface area over the volume of the extracted tumor. The results for the clinical cases of three malignant and two benign tumors are successfully obtained by the system using an ultrasonic mechanical sector-scanning probe of 10 MHz. It is found that the differences in the surface roughness between both types of tumors are clearly evident using a rendered surface image of the extracted tumor, and the average value of the defined parameter for the above three malignant is 9.6, and 3.8 for the benign.

BRIEF DESCRIPTION OF THE DRAWINGS

FIG. 4A is an ultrasonic image of breast tumor.

FIG. 4B shows a zx-plane image of the formed voxel data.

FIG. 20 shows the examples of tumor diagnosis carried out with the system of present invention in the clinical practice.

FIG. 21A shows the boundaries of the extracted benign tumor, and

FIG. 21B shows the image of zx-plane in voxel data superimposed, and a computer rendered 3D-image of the extracted tumor in case no.1.

FIGS. 30A and 30B show the boundaries of the extracted benign tumor and the image of zx-plane in voxel data superimposed, and a computer rendered 3D-image of the extracted tumor in case no.27, respectively.

FIG. 31 shows the results of the application of the algorithm to clinical cases.

DETAILED DESCRIPTION

Figure 1:
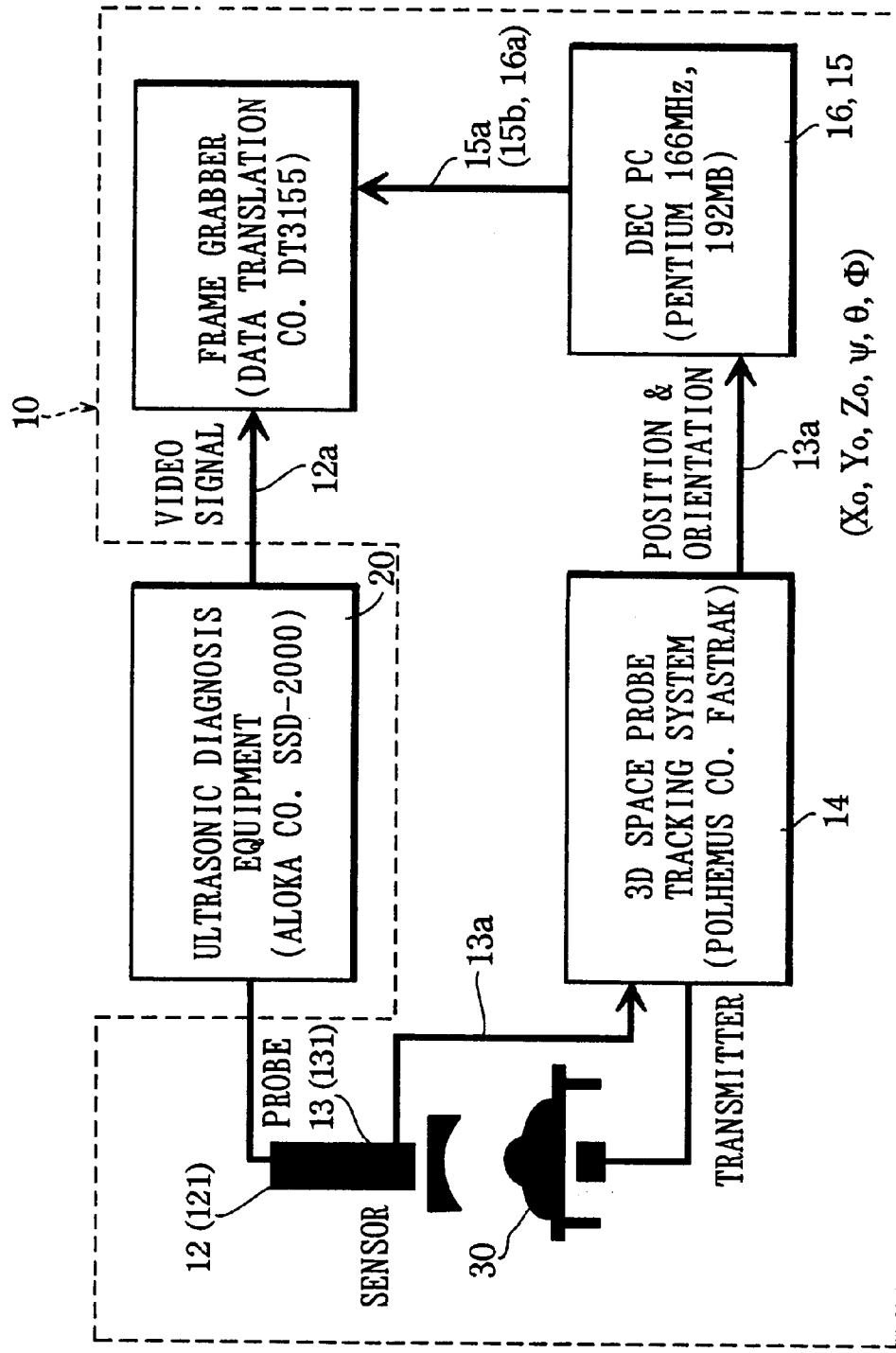
FIG. 1 is a block diagram of the 3D-ultrasonic image capturing system.

The Outline of the Breast Cancer Diagnosis System

In ultrasonic echographic image (ultrasonic echographic cross sectional image data), intensity of image of the breast tumor is lower than that of normal tissues), so that tumor can be extracted based on the intensity of image of the breast tumor.

It is, however, difficult to extract a target from the ultrasound images by a conventional image processing such as simpler binary digit processing method due to the artifacts of speckle noise and acoustical shadows, and some existing low intensity regions such as blood vessels, and so on.

In this embodiment describes tumor auto extract diagnostic method (process) and apparatus for finally determining tumor region by classifying voxel data of the tumor as "tumor", "normal tissue" or "boundary" by solving three-dimensional (3D) contradiction.

This algorithm is attributable to 3 steps of operation:

In $1^{st}$ step [3D image obtaining process], ultrasonic probe with three-dimensional (3D) coordinates detector (probe attitude detect sensor) obtains the ultrasonic echographic image (ultrasonic echographic cross sectional image data 121a).

In $2^{nd}$ step [tumor extract process], automatically generating a membership function $\{\mu_t, \mu_n, \mu_b\}$ used in the fuzzy reasoning, carrying out fuzzy reasoning operation and defuzzifying operation for each of voxels datum so as to extract voxel data that has probability of being malignant tumor are carried out so as to discriminate malignant tumor region.

$3^{rd}$ step [a malignant tumor auto discriminating process], discriminating a degree of surface roughness of a tumor, extracting a boundary between tissues to find breast cancer tissues out of the tissues based on the voxel data 16a, 3D image data, from two dimensional cross sectional image such as MRI image or ultrasonic image. In most of case, breast tumor occurs quite near to the surface of the body.

Prevention and early diagnosis of breast cancer are of foremost importance. Since there are various kinds of tumors in the mammary, it is quite important to discover tumors smaller than 1 cm or less as early as possible, so as to diagnose weather the tumor is malignant or benign.

Consequently, the object of this embodiment is far smaller than an embryo or heart, and located near the skin of the patient's body, it must be carried out quite carefully to contact a ultrasonic probe with the surface of the body (or object). Therefore, manual scanning method and mechanical scanning method, both scanning method have some problem respectively.

Manual scanning method cannot or difficult to achieve high accuracy, and mechanical scanning method cannot or difficult to follow or sometimes roughly touches on the surface of the body of a patient. So, in this embodiment, three dimensional (3D) position sensor using alternate magnetic field technology is attached to the ultrasonic probe 121 to obtain 3D coordinates data and ultrasonic echographic image (ultrasonic echographic cross sectional image data 121*a*) respectively at a time (synchronized) with inspector scanning the scanner and observing the ultrasonic image.

The ultra sonic 3D-image of voxel data 16*a* is constructed by using 3D-interpolation method referring to the 3D coordinates.

3D-coordinates data and ultrasonic echographic image (ultrasonic echographic cross sectional image data 121*a*) is affected by the echo of objects of the body such as subcutaneous fat, organs or other tissues surrounding the tumors, so that each patients has a different arithmetic value such as average value of the image intensity, distribution, and so on.

Therefore, it is required to readjust or to change the gain of diagnostic system or STC (Sensitivity Time Control) or TGC (Time Gain Compensation) according to the physical individuality when practicing the diagnosis.

Consequently, in such a manner described above, tumor diagnosis system has to correspond to the change.

In this embodiment, method and system can generate membership function $\{\mu_t, \mu_n, \mu_b\}$ corresponding to each image using three dimensional LoG(Laplace of Gaussian) filter so as not to depend on the system environment. This method generates automatically the membership function $\{\mu_t, \mu_n, \mu_b\}$ for each index such as distance between center of gravity of intensity and morphological center or distance between center of variance of intensity and morphological center correspond to histogram of classified voxel data such as "tumor", "normal tissue", or "boundary" by using the output from the LoG filter. And it should be mentioned specifically that the membership function is generated based on approximation method using Reyleigh distribution and Gaussian distribution.

And then, tumor region is extracted employing the auto generated membership function $\{\mu_t, \mu_n, \mu_b\}$ In this step, at first, generating images which represents 3 classified grade {t, n, b} respectively by fuzzy reasoning; such as "tumor", "normal tissue" or "boundary".

Then, carrying out a defuzzifying process according to relaxation method to classify every voxels into the three classes described above.

For misjudged (misclassifyed) voxels, making some amendment based on some previous known information to determine three-dimensional region of the tumor must be performed.

And the last step shows that the extracted tumor is displayed as a 3D image in surface rendering.

On the other hand, surface roughness of the extracted tumor is evaluated by ratio; cube of surface space($S^3$)/square of volume($V^2$) of the extracted tumor.

Consequently, according to this embodiment, both types of tumors can be well extracted when the system of this embodiment is used practically (clinically) in 16 (malignant case) and in 11(benign case) shown in FIG. 20.

And according to present invention, it is well expected to diagnose tumors whether malignant or benign, by evaluating the surface of the tumors in such a manner approximately described above.

The Outline of Breast Cancer Diagnosis System

FIG. 1 shows the block diagram of the breast cancer diagnosis system (apparatus).

An alternate magnetic sensor (Fastrak by Polhemus Co.) is equipped on the ultrasonic probe to track the position and the orientation of the probe while it manually scans over the breast.

The ultrasonic image data 121*a* and the position and the orientation of the probe are transferred into the RAM of PC15, 16 20 (DEC Pentium 166 MHz, 192 MB(trade name)) through a PC15,16I Bus frame grabber(trade name, Data Translation Co. DT3155) at a rate of 15 frames per second (f/s) and RS232C, respectively.

The captured ultrasonic images are then transformed into the three-dimensional voxel data 16*a*. And most of operation and calculation concerning with the fuzzy reasoning and defuzzification process carried out in the PC15, 16

Figure 5:
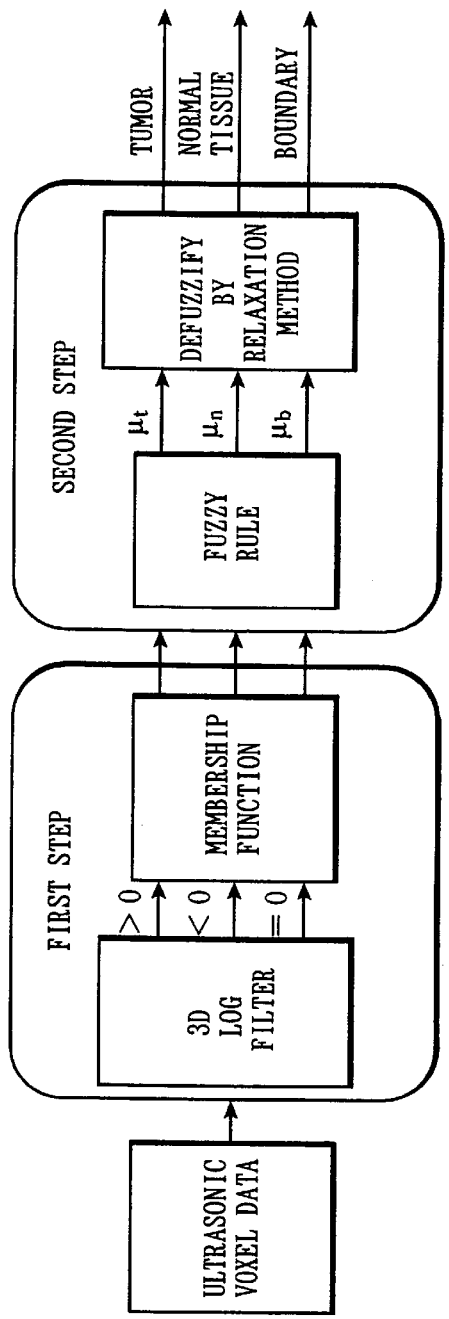
FIG. 5 shows the scheme of the proposed method employing fuzzy reasoning.
Figure 8:
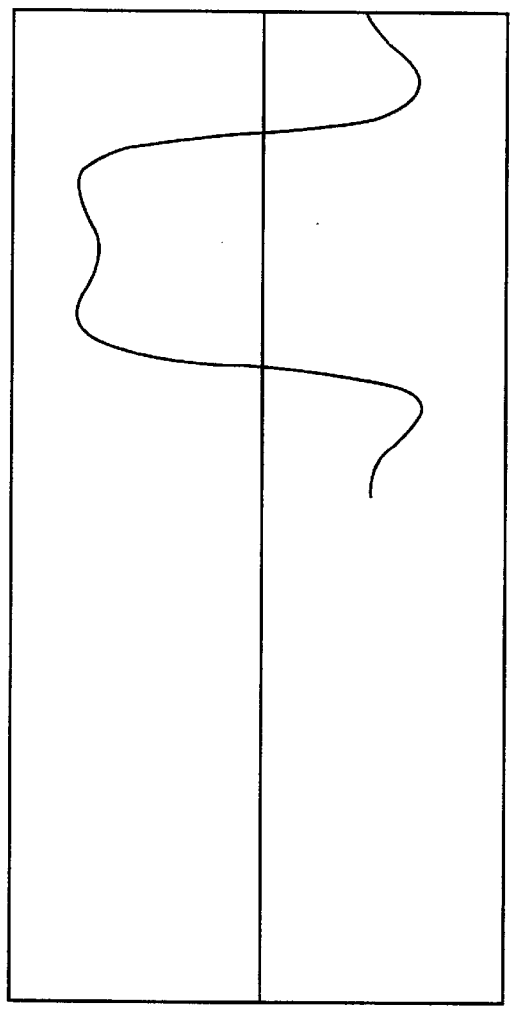
FIG. 8 is the profile of output of 3D-LoG(Laplace of Gaussian) filtering for a sphere model.

FIG. 5 shows the scheme of the proposed method employing fuzzy reasoning.

It is divided into two stages (steps) of processing. In the first stage, a membership function for fuzzy reasoning is determined by pre-classified voxel data. In the second stage every voxel is classified into three types of classes that are "tumor", "normal tissue", and "boundary". According to the $1^{st}$ stage, tumor extraction can be carried out independent on system environment.

Figure 7:
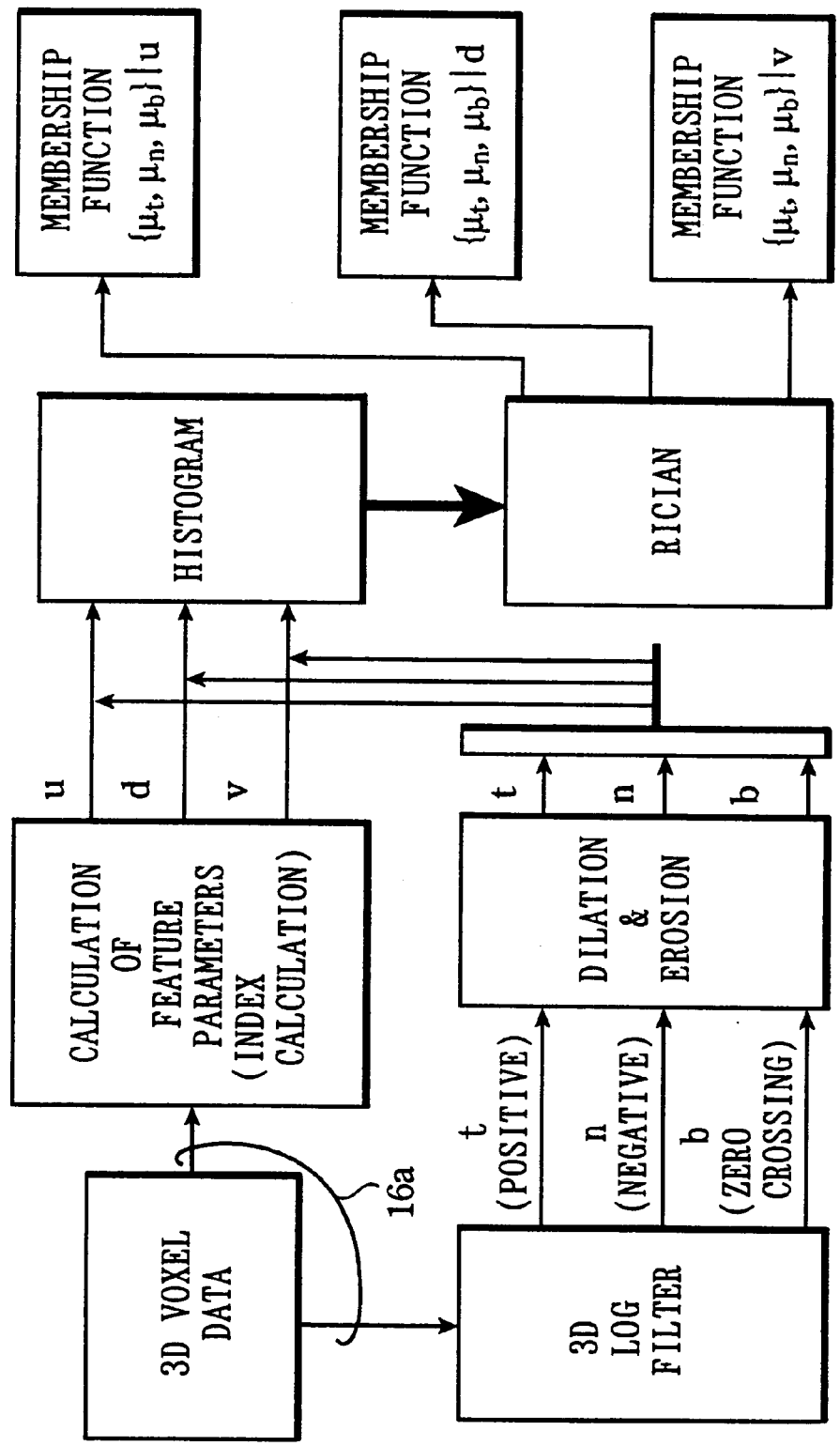
FIG. 7 shows the block diagram of the first stage.

FIG. 7 shows the block diagram of the first stage.

Figure 6:
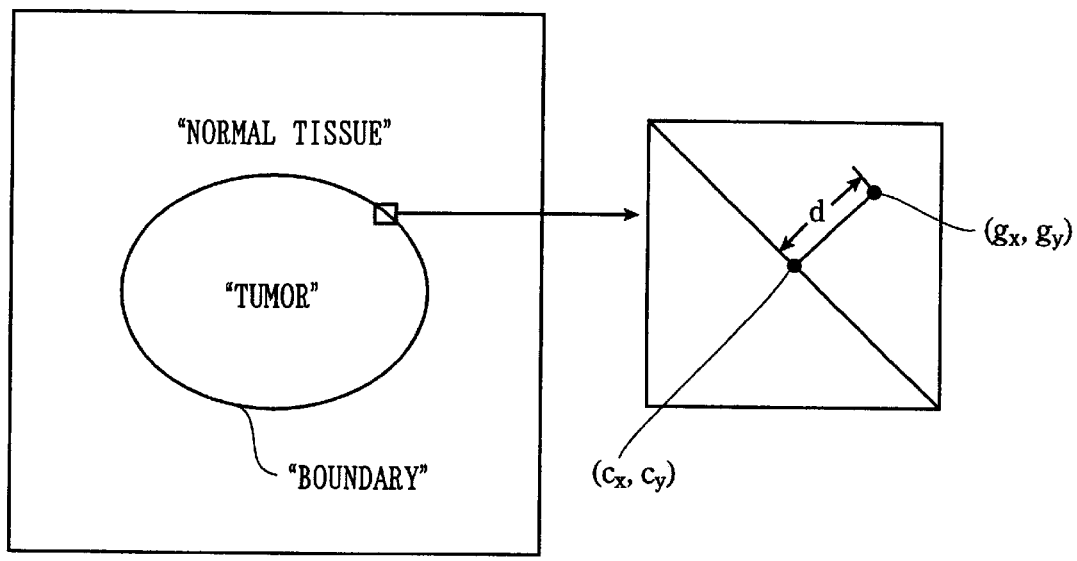
FIG. 6 shows a concept of the feature parameter d shown in 2D case.

And FIG. 6 shows a concept of the feature parameter d shown in 2D case. Where, (Cx, Cy) is the morphological center of the reference region, and (Gx, Gy) is the center of gravity of the reference region. If an interest voxel is "boundary", the value of d is larger, otherwise d is smaller.

It must be noted that low intensity areas and high intensity areas are confused within a tumor region.

Therefore, in general, value d of normal tissue and of boundary are to some extent overlap.

A three dimensional LoG(Laplace of Gaussian) filter is used for generation of the membership function. The filter is expressed as, $$g(r)=(r^2-3\sigma^2)/\{(2\sigma^3)^{1/2}\sigma^7\}\exp(-r^2/2\sigma^2),$$

where r is a distance from the origin and σ is the standard deviation of the Gaussian.

A feature of the breast tumor is that it is displayed in the ultrasonic image as lower level of intensity than the surrounding normal tissue. The output values of LoG filtering have the following meanings. The zero-crossings are correspondent to the contour.

The positive values mean that the region is correspondent to a darker area. The negative values mean that the region is correspondent to a brighter area. The voxel in the darker area has a higher degree for "tumor". The voxel in the brighter area has a higher degree for "normal tissue". Three kinds of statistical parameters for the three classes of "tumor", "normal tissue" and "boundary" are used for fuzzy reasoning. All the parameters is computed in a volume of 7×7×7 voxel. They are the local intensity mean u, the distance d between the center of intensity gravity and the morphological center of the volume, and the deviation of intensity v.

One of the approaches to define a membership function is to use the probability density function that is calculated by the voxel data classified as the three types. A probability density function of the brightness of ultrasound image is defined as Rician density function, $$P_A(x)=x/\sigma^2 \exp\{-(x^2+s^2)/2\sigma^2\}I_0(xs/\sigma^2) \quad (2),$$

where $I_0(x)$ is modified Bessel function of the first kind, zero order. As s increases, The shape of the Rician density function changes from that of a Rayleigh density function to that of the function to be approximately a Gaussian density with mean equal to s. Rician density function is considered as one of the definition of the membership function. The membership function of u for "boundary" and "normal tissue" is approximated by Gaussian, and that for "tumor" is approximated by Rayleigh density. That of d and v is approximated by a Rayleigh density.

In the second stage a fuzzy reasoning and defuzzification are used for the classification of the three types of biological tissues. The rule for fuzzy reasoning is defined as follows.

If (u is small) and (d is medium) and (v is small) Then the voxel is "tumor"

If (u is large) and (d is medium) and (v is large) Then the voxel is "normal tissue"

If (u is medium) and (d is large) and (v is medium) Then the voxel is "boundary" (3).

Let $\mu_t,\mu_n,\mu_b$ be the grades which attribute to the three types of classes of "tumor","normal tissue" and "boundary". And let $\mu_{t|u},\mu_{t|d},\mu_{t|v},\mu_{n|u},\mu_{n|d},\mu_{n|v},\mu_{b|u},\mu_{b|d},\mu_{b|v}$ be the grades for each statistical parameter, which are obtained by the membership function. The following expression is thus obtained.

$$\mu_t=\min\{\mu_{t|u}, \mu_{t|d}, \mu_{t|v}\}$$

$$\mu_n=\min\{\mu_{n|u}, \mu_{n|d}, \mu_{n|v}\}$$

$$\mu_b=\min\{\mu_{b|u}, \mu_{b|d}, \mu_{b|v}\} \quad (4)$$

Accordingly, three types of images $\{\mu_t,\mu_n,\mu_b\}$ representing the grade of each voxel attributable to the three classes for all the voxel data are computed.

A classification of each voxel as one of the three classes of "tumor","normal tissue" and "boundary" is made by applying a relaxation technique to the images $\{\mu_t,\mu_n,\mu_b\}$. In our approach, the "boundary" is defined as a "normal tissue" which is adjacent to the "tumor". That is, 1) if a voxel is "tumor", it is not adjacent to "normal tissue"; 2) if a voxel is "normal tissue", it is not adjacent to "tumor"; 3) if a voxel is "boundary", it must be adjacent to both of the "tumor" and the "normal tissue".

Let $N_t,N_n,N_b$ be the number of voxel in the 3×3×3 voxel volume, which is counted by the voxel having the largest value among $\{\mu_t,\mu_n,\mu_b\}$. Expression (5) shows the constraints for our defuzzification processing.

R1: if $N_t>=1$ and $N_b>=2$ and $N_n>=1$ then $\mu_t--, \mu_n--, \mu_b++$

R2: else if $N_n=0$ and $N_b>=1$ and $N_t>=1$ then $\mu_t++, \mu_n--, \mu_b--$

R3: else if $N_t=0$ and $N_b>=1$ and $N_n>=1$ then $\mu_{n++}, \mu_n++ \mu_b--$

R4: else if $N_t>N_n+12$ then $\mu_t++, \mu_n--, \mu_b--$

R5: else if $N_n>N_t+12$ then $\mu_t--, \mu_n++, \mu_b--$

R6: else Then $\mu_t--, \mu_n--, \mu_b++$ (5), where, the sign of "++" means that a constant C will be added to the corresponding grade, and the sign of "--" means the grade is decreased by C.

The defuzzification is computed by a relaxation method under the constraints of expression of (5). A region of "tumor" is extracted by the iterative processing.

A characteristic of a malignant tumor is that the surface appears as uneven complex shapes. This geometrical characteristic is evaluated in our system by a parameter defined in (6).

$$r=(S^3/V^2)/36\pi \quad (6),$$

where S stands for the surface area, and V for the volume of the region of "tumor". The coefficient of 1/36 π is a normalizing factor. The parameter of r is equal to 1.0 when a tumor is a sphere. The larger r is the more the roughness of the surface is and the smaller it is, the more the smoothness of the surface is.

Three-dimensional Image Obtaining Process

Figure 3:
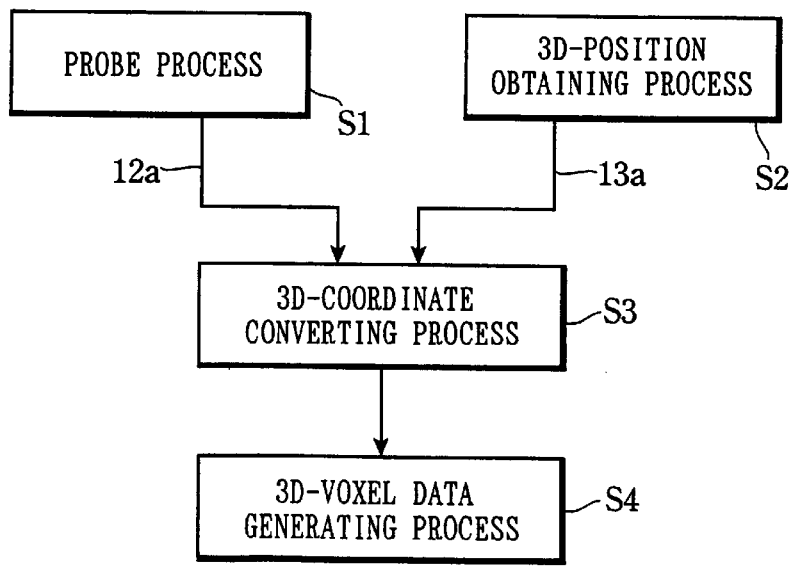
FIG. 3 is a flowchart of the 3D-image obtaining process.

FIG. 3 shows a flow chart of the 3D-image obtaining process described below, which has prove process, 3D-position sensor process S2, 3D-coordinates converting process S3 and 3D-voxel data generating process S4.

This process significant in 3D(three-dimensional) image data operation. In this process, probe mean, ultrasonic probe, 3D position sensing mean, alternate magnetic sensor 131, ultrasonic diagnosis apparatus and tracking mean 14 showed in 494 the FIG. 1

This process is carried out as follows;

Ultrasonic cross sectional image data 121a obtaining process obtains ultrasonic cross sectional image, with a probe(using ultrasonic probe; 7.5 MHz, hollow type) for generating voxel data concerned with inner structure and surface structure of surface of a mammal gland. And a 3D-position sensor process S2 measuring coordinates of probe used therein and/or attitude of the probe and generating probe coordinates data of the probe synchronized with movement of the probe.

3D-position sensing mean (or alternate magnetic sensor) is attached to the probe measures coordinates of probe($x_0$, $y_0,z_0$) used on the body over the mammary glands and/or attitude of the probe($\psi,\Phi,\theta$) and generating probe coordinates data of the probe($x_0,y_0,z_0,\psi, \Phi, \theta$) synchronized with movement of the probe.

Tracking mean 14 collects the probe coordinate data synchronized with the collection of the probe data. So it can be the that low artifact and high precision 3D voxel data.

Figure 2:
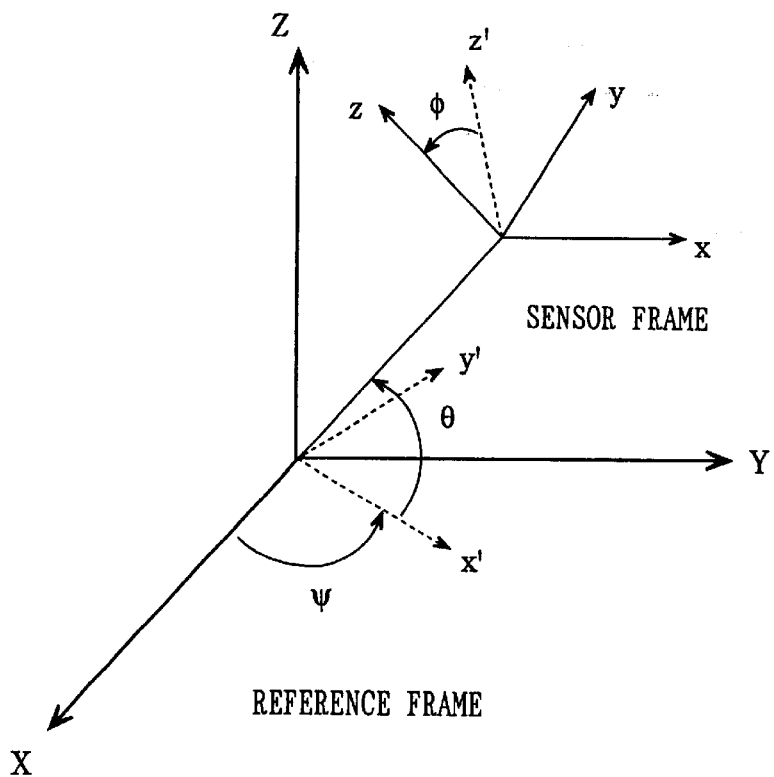
FIG. 2 is a 3D-space coordinate system.

FIG. 2 shows the angle and coordinates described above. 3D-voxel data generating mean used the 3D-voxel data generating process S4 is constructed in the PC15, 16.

3D-coordinates converting mean employing matrix $T[a_{ij}]$ (i,j=1,2,3), bearing angle $\psi$, angle of elevation $\theta$, and lateral angle $\Phi$ in the probe process S1. So the consequence is that the 3D coordinates converting mean can generate a set of coordinates (x',y',z') as the probe coordinates data by operating a product of the probe data's coordinates(x,y,0) and the matrix with high speed and high cost performance ,even with smaller systems. As the PC15, 16, DEC Pentium 166 MHz, 192MB(trade name)) is used, and OS is Windows 95(trademark)). The Fastrack tracking system 14 calculates the 3D position data by using usual method of generating and Receiving the alternative magnetic field. And the position data is sent to the PC15, 16 by using RS232. The program for carrying out the 3D-image obtaining process is stored at the memory mean in the PC15, 16 such as EEP-memory. Or installed in the PC15, 16 through Internet, or stored in some magnetic memory mean.

And the probe data and the 3D-coordinates data is generated at the ultrasonic diagnosis apparatus followed by a process of A/D conversion, and then, directly memorized in the memory mean in PC15,16. So, collecting image data can be quite fast by using this system and method.

In this 3D-image obtaining process, a probe data obtaining process with a probe scanning over an object to generate probe data concerned with inner structure and surface structure of surface of an object.

3D-position sensor process S2 measuring coordinates of probe used therein and/or attitude of the probe and generating probe coordinates data of the probe synchronized with movement of the probe.

Tracking process for collecting the probe coordinates data with the probe data synchronized therewith; a 3D-coordinates converting process S3 for generating 3D-image data by using the probe data and the probe coordinates data.

3D-voxel data generating process S4 carrying out linear interpolation for the 3D image to convert the 3D image data into an equilateral voxel data, and when plural of values are correspond to one voxel, generates the voxel data by calculating an average value of the plural values.

Probing process with a probe for generating probe data concerned with inner structure and surface structure with scanning surface of mammal glands.

3D-position sensor process S2 measuring coordinates of probe used on the body over the mammary glands and/or attitude of the probe and generating probe coordinates data of the probe synchronized with movement of the probe.

Tracking process for collecting the probe coordinates data with the probe data synchronized therewith; 3D-coordinates converting process S3 for generating 3D image data by using the probe data and the probe coordinates data.

3D-voxel data generating process S4 carrying out linear interpolation for the 3D image to convert the 3D image data into an equilateral voxel data, and when plural of values are correspond to one voxel, generates the voxel data by calculating an average value of the plural values.

The 3D-coordinates conversion process employing matrix $T[a_{ij}]$ (i,j=1,2,3), bearing angle $\psi$, angle of elevations $\theta$, and roll angle $\Phi$ in the probe process S1 so as to generate a set of coordinates(x',y',z')=Q as the probe coordinates data by operating a product of the probe data's coordinates(x,y,0)=P, and the matrix. And R is defined as $(x_0,y_0,z_0)$=R,Q is calculated as; $Q^t = TP^t + R^t$ wherein, $Q^t$ means a translation of matrix Q.

The 3D-coordinates each elements in the matrix $T[a_{ij}]$ in 3D coordinates conversion process are defined as follows:

$a_{11} = \cos(\psi)\cdot\cos(\theta)$
$a_{12} = \cos(\psi)\cdot\sin(\theta)\cdot\sin(\Phi) - \sin(\psi)\cdot\cos(\Phi)$
$a_{13} = \cos(\psi)\cdot\sin(\theta)\cdot\cos(\Phi) + \sin(\psi)\cdot\sin(\Phi)$
$a_{21} = \sin(\psi)\cdot\cos(\theta)$
$a_{22} = \cos(\psi)\cdot\cos(\Phi) + \sin(\psi)\cdot\sin(\theta)\cdot\sin(\Phi)$
$a_{23} = \sin(\psi)\cdot\sin(\theta)\cdot\cos(\Phi) - \cos(\psi)\cdot\sin(\Phi)$
$a_{31} = -\sin(\theta)$
$a_{32} = \cos(\theta)\cdot\sin(\Phi)$
$a_{33} = \cos(\theta)\cdot\cos(\Phi)$ In this process described above, it is necessary to obtain 3D-image data. So, at first, carry out 3D-conversion on a plural of set of cross sectional images, and then, convert them to the voxel data by an interpolation. For this conversion, there are several kinds of method. I.e., 1. Nearest Neighbor Interpolation (NNI).
2. Linear Interpolation (LI).
3. Cubic Convolution Interpolation (CCI).

NNI is an easier method, but cannot work well in case of low grayscale tone.

LI is such a method deciding a value of intensity in proportion to distance between voxels (or pixels). Easier operation and can achieve the smoothness of voxel arrangement.

CCI is a method using 16 voxels around the voxel of interest. Easier operation but does not work well when there exists some speckle noise or artifact.

So in this embodiment of the invention, employing LI. And process described above achieves high-speed operation and the smoothness of voxel arrangement.

Figure 4A:
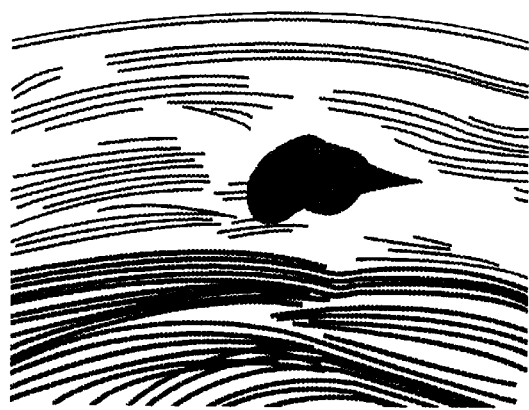
FIGS. 4A and 4B are examples of the voxel data formed by a 3D-coordinate transmission and interpolation.
Figure 4B:
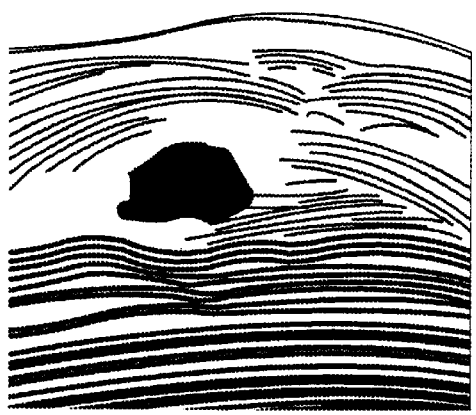

FIGS. 4A and 4B show images obtained by the image obtaining process. In FIG. 4A is a cross sectional ultrasonic image of tumor in mammary gland and FIG. 4B is an image of a voxel data in a zx plane. In those images, low intensity area is represents tumors and the surroundings around the tumor normal tissues are shown.

Tumor Extracting Process

It is significant for displaying and evaluating a 3D-morphological surface of a tumor to extract tumor region from a plural of ultrasonic image. Because 3D-image helps quite effectively the inspector to find the tumors visually.

But in a mammary gland, there exists speckle noise and/or artifact, so that problem such as lack of boundary and/or low intensity region occurs.

In this respect, binary image method and differential operation could not achieve fine imaging enough to support precise diagnosis.

But on the other hand, the system and method used in this embodiment of the present invention can achieve well working extraction by employing the extract process in 3D-space.

FIG. 5 shows the scheme of the proposed method employing fuzzy reasoning. This algorithm has two stages written in a program code that can be carried out by the PC15, 16.

Figure 15:
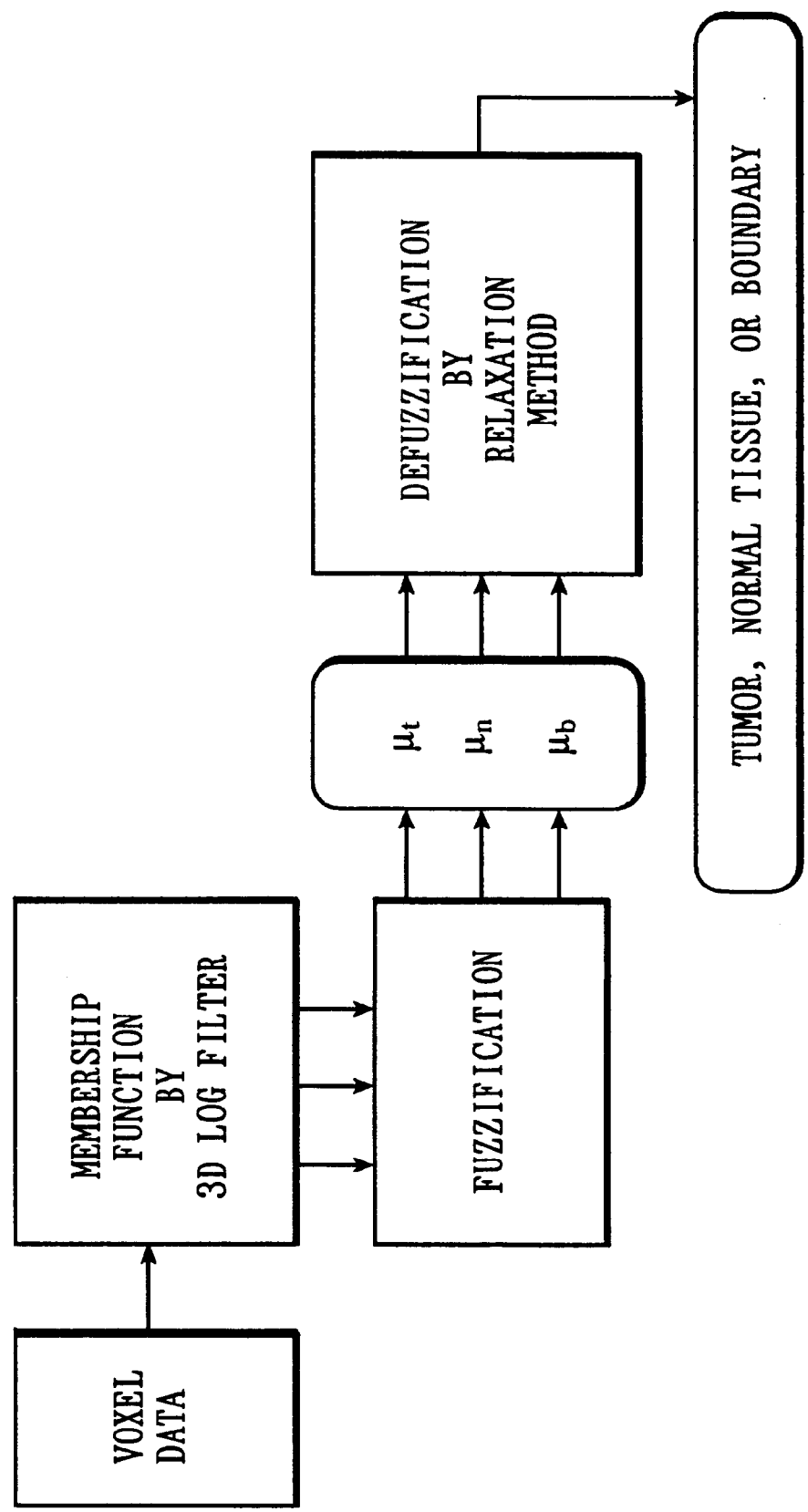
FIG. 15 shows the scheme of the breast tumor extraction algorithm employing fuzzy reasoning.

FIG. 15 shows the scheme of the breast tumor extraction algorithm employing fuzzy reasoning.

Figure 17:
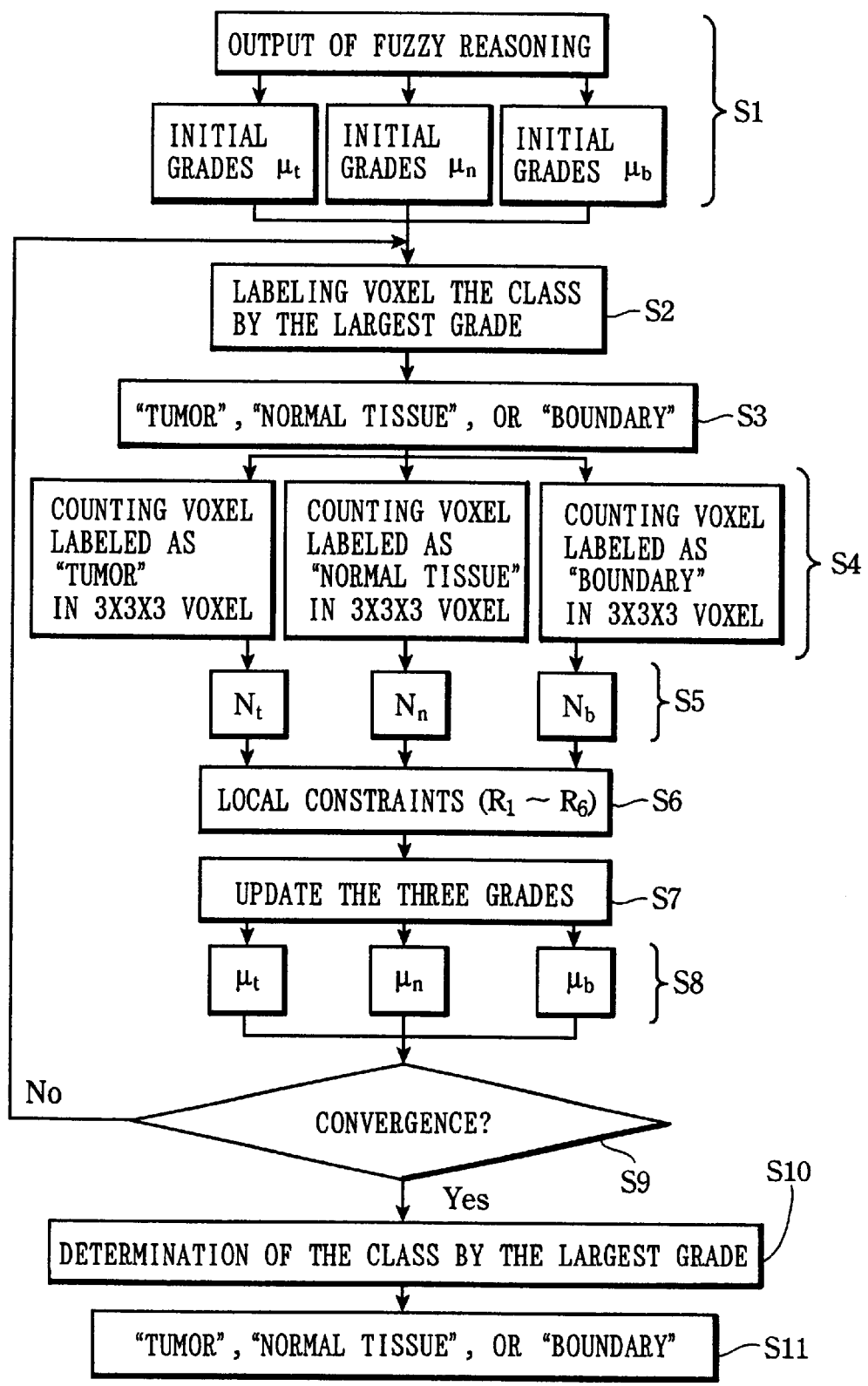
FIG. 17 is a flow of procedure of the determination of "tumor", "normal tissue" and "boundary" by relaxation method, i.e., defuzzifying process.

And FIG. 17 is a flow of procedure of the determination of "tumor", "normal tissue" and "boundary" by relaxation method, i.e., defuzzifying process.

This tumor extract process carrying out fuzzy reasoning operation and defuzzifying operation for each of the voxels datum so as to extract voxel data that has probability of being malignant tumor so as to discriminate malignant tumor region.

And the tumor extract process further comprises processes and algorithms as follows:

Operating index process for operating uneven complexity of the surface roughness expresses arithmetic volume distribution which concerning tumor regions, normal tissues and tumor boundary between the tumor regions and normal tissues on a ultrasonic echographic image of each three dimensional voxels as probability distribution in [0,1] region of membership function which is employed a fuzzy reasoning.

And generating membership function process that includes process for extracting automatically the tumor region by arranging the arithmetic volume distribution according to fuzzy reasoning that employs the membership function.

Fuzzy reasoning process for classifying the each voxels into predetermined plural of types of region according to the generated membership function and fuzzy rules thereof.

Defuzzifying process for defuzzifying and finally determining tumor region by classifying the voxel as "tumor", "normal tissue" or "boundary";

And the arithmetic volume includes an average value of intensity and a distribution of intensity of the voxel;

The intensity=$\{\ddagger\ddagger\ddagger f(I,j,k)\}/N^3$, while, I,j,k=0,1,2...N−1 (N=natural number), and the f(I,j,k) represents a value of intensity of voxel volume and t is a mathematical symbol;

The arithmetic volume includes an average value of intensity and a distribution of intensity of the voxel; the center of the intensity of gravity of the voxel$(g_x,g_y,g_z)$ is given as follows:

$g_x=\{\ddagger\ddagger\ddagger\{f(i,j,k)\cdot(i+1)\}\}/\{\ddagger\ddagger\ddagger f(i,j,k)\}$
$g_y=\{\ddagger\ddagger\ddagger\{f(i,j,k)\cdot(j+1)\}\}/\{\ddagger\ddagger\ddagger f(i,j,k)\}$
$g_z=\{\ddagger\ddagger\ddagger\{f(i,j,k)\cdot(k+1)\}\}/\{\ddagger\ddagger\ddagger f(i,j,k)\}$ Distance(d) between the center of the intensity of gravity and the morphological center in each the voxels is given as follows:

$d=\{(g_x-c_x)^2+(g_y,-c_y)^2+(g_z-c_z)^2\}^{1/2}$, while, I,j,k=0,1,2... N−1 (N=natural number), the f(I,j,k) represents a value of intensity of voxel volume and $\ddagger$ is a mathematical symbol, N is a volume of voxel of interest, u is an averaging value of intensity of voxel.

And the membership function auto generating process generates the membership function used in the fuzzy reasoning for each of the voxels based on an output of 3Dgaussian-Laplace filter in case that arithmetic value including distribution of intensity on a ultrasonic image of mammary gland has any change caused by subcutaneous fat thickness or mammary glands of the body of a patient.

The membership auto generating process further comprising:

Three-dimensional(3D) LoG filter process obtaining 3D-Gaussian-Laplace filter g(r) given by
$g(r)=(r^2-3\sigma^2)/\{(2\sigma^3)^{1/2}\sigma^7\}\exp(-r^2/2\sigma 2)$ where r is a distance from the origin and $\sigma$ is the standard deviation of the Gaussian.

Boundary extracting process extracting "boundary" of objective region by tying zero(0) crossing points together;

Tumor extracting process classifying voxel which has positive value output attributed to low intention voxel from the 3DloG filter as "tumor".

Normal tissue extracting process classifying voxel which has negative value output attributed to high intention voxel from the 3D-LoG filter as "tumor".

Dilation and erosion process carrying out dilation and erosion
for the classified "tumor" voxel to get rid of voxels which exists isolated in a normal tissue and/or to get rid of voxels classified as "boundary", and in case that the classified "tumor" voxel is tied with any other low intensity regions, to divide the classified "tumor" voxel from the other low intensity regions;

Voxel selecting and index value calculating process carrying out the operating index process for voxels which classified as "boundary" to obtain the average value of intensity, the distance, and the distribution of intensity;

Membership function determining process determining plural of the membership function for three kinds of the index values obtained in the voxel selecting and index value calculating process respectively corresponding to probability density function.

Figure 10:
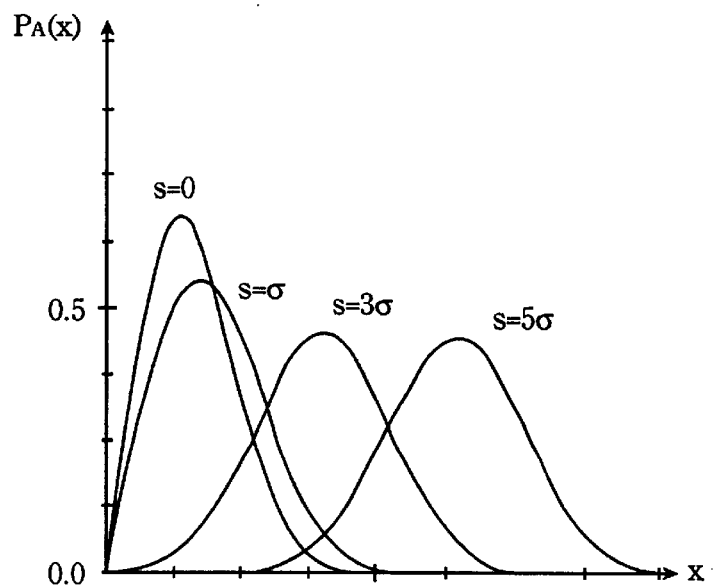
FIG. 10 shows graph of Rican density function.

FIG. 10 shows graph of Rican density function. it is known that probability density index of intensity of ultrasonic image expressed as follows;

$P_A(x)=x/\sigma^2 \exp\{-(x^2+s^2)/2\sigma^2\}I_0(xs/\sigma^2)$, where $I_0(x)$ is modified Bessel function of the first kind, zero order.

In the membership function determining process, the membership function is approximated by Reyleigh density function in case of "tumor", or the membership function is approximated by Gaussian density function in case of "normal tissue" or "boundary", In the membership function determining process, the membership which correspond to the distance is approximated by Reyleigh density function;

And in the membership function determining process, the membership which correspond to the distribution of intensity is approximated by Reyleigh density function.

The fuzzy reasoning process further having a process for carrying out classifying each of plural of the voxel into three grades such as "tumor" grade, normal tissue grade and "boundary" grade, by employing the membership function and fuzzy rules generated in the fuzzy reasoning process;

And the fuzzy rules are expressed in "if then else" rules defined as follows:

If (u is small) and (d is medium) and (v is small) Then the voxel is "tumor"

If (u is large) and (d is medium) and (v is large) Then the voxel is "normal tissue"

If (u is medium) and (d is large) and (v is medium) Then the voxel is "boundary"

Wherein, u is the average value of intensity, d is the distance and v is the distribution of intensity.

The fuzzy reasoning process further has:

1st logic process obtaining 3 grades expressed as follows:
Letting $\mu_t, \mu_n, \mu_b$ be the grades which attribute to the three types of classes of "tumor", "normal tissue" and "boundary", letting $\mu_{t|u}, \mu_{t|d}, \mu_{t|v}, \mu_{n|u}, \mu_{n|d}, \mu_{n|v}, \mu_{b|u}, \mu_{b|d}, \mu_{b|v}$ be the grades for each statistical parameter, which are obtained by the membership function.

2nd logic process obtaining analogical value $\mu_t$ attributable to "tumor", $\mu_n$ attributable to "normal tissue", $\mu_b$ attributable to "boundary", so as to obtain the three types of images $\{\mu_t, \mu_n, \mu_b\}$ representing the grade of each voxel attributable to "tumor", the three classes for all the voxel data by imputing the grades obtained in 2nd logic process, thus obtained values are expressed respectively as follows:

R1: $\mu_t = \min\{\mu_{t|u}, \mu_{t|d}, \mu_{t|v}\}$

R2: $\mu_n = \min\{\mu_{n|u}, \mu_{n|d}, \mu_{n|v}\}$

R3: $\mu_b = \min\{\mu_{b|u}, \mu_{b|d}, \mu_{b|v}\}$ wherein, $\min(a_1, a_2, a_3)$ means an operation selecting a minimum among the $a_1, a_2, a_3$.

The defuzzifying process for defuzzifying each of plural of the voxels further comprising:
defining process which defines rules as follows:
1) if a voxel is "tumor", it is not adjacent to "normal tissue";
2) if a voxel is "normal tissue", it is not adjacent to "tumor";
3) if a voxel is "boundary", it must be adjacent to both of the "tumor" and the "normal tissue".

when classifying all of the voxel data based on three classified image $\{\mu_t, \mu_n, \mu_b\}$ by relaxation method.

Figure 11:
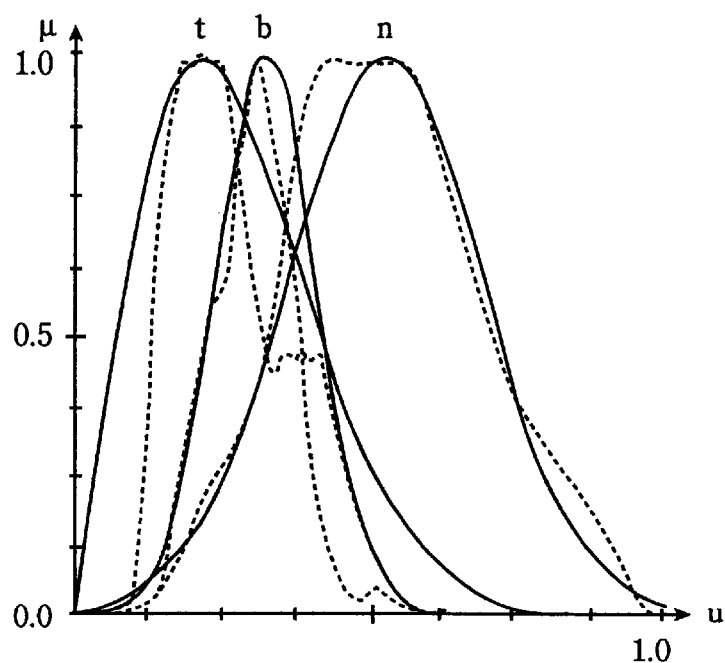
FIG. 11 shows membership function (solid curve) and histogram (dashed curve) for parameter u.

FIG. 11 shows membership function (solid curve) and histogram (dashed curve) for parameter u. Those curves are approximately coincident.

Figure 12:
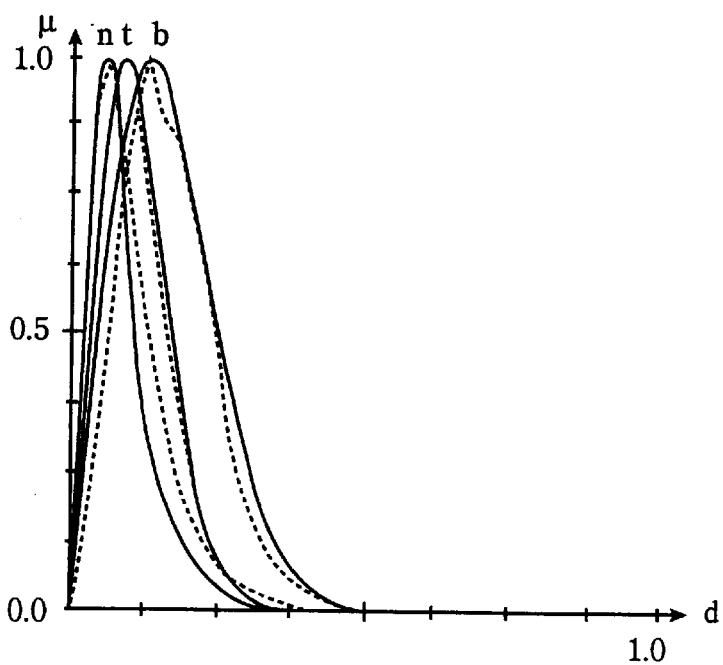
FIG. 12 shows membership function (solid curve) and histogram (dashed curve) for parameter d.
Figure 14:
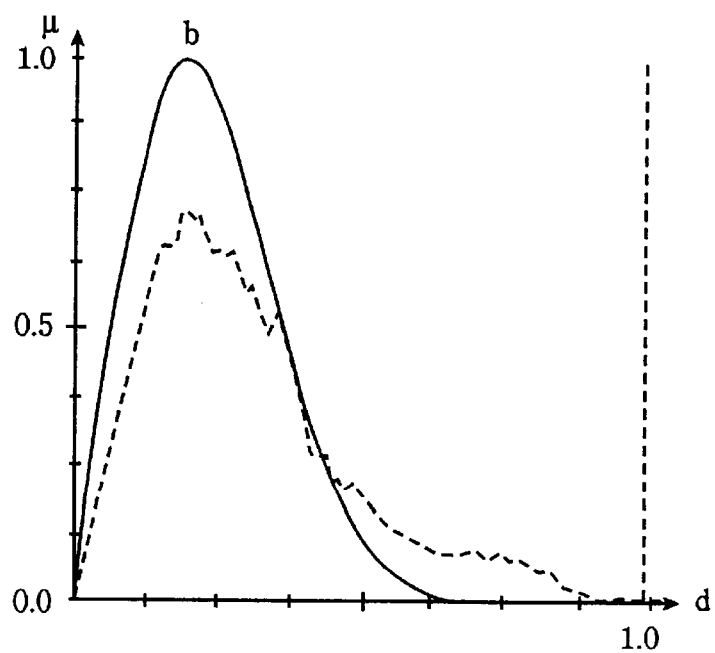
FIG. 14 is Rayleigh distribution.

FIG. 12 shows membership function (solid curve) and histogram (dashed curve) for parameter d. It should be noted that Rayleigh distribution resembles to the histogram for parameter d. Therefore in present invention, Rayleigh distribution is employed, as shown in FIG. 14.

Figure 13:
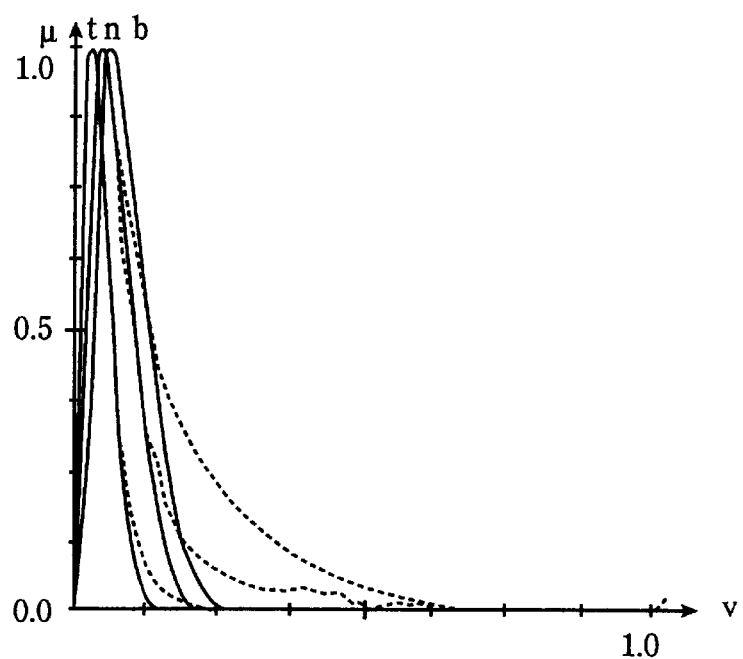
FIG. 13 shows membership function (solid curve) and histogram (dashed curve) for parameter v.

FIG. 13 shows membership function (solid curve) and histogram (dashed curve) for parameter v. It should be noted that Rayleigh distribution resembles to the histogram for parameter v. therefore in present invention, Rayleigh distribution is employed.

Figure 9A:
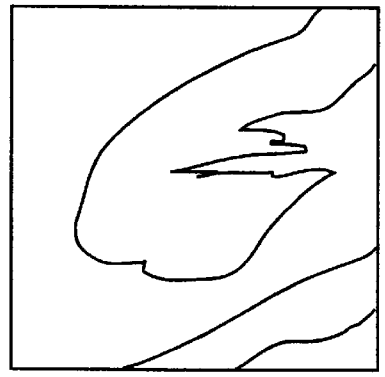
FIGS. 9A, 9B and 9C show a cross sectional image of a malignant tumor, a normal tissue and the boundary, respectively.
Figure 16A:
FIGS. 16A, 16B and 16C show the images of "tumor($\mu_t$)", "normal tissue($\mu_n$)", "boundary($\mu_b$)" obtained by means of the fuzzy reasoning of present invention, which correspond to the voxel of "tumor" shown in FIG. 9A.
Figure 16B:
Figure 16C:

FIGS. 16A to 16C show the images of "tumor$(\mu_t)$", "normal tissue$(\mu_n)$", "boundary$(\mu_b)$" obtained by means of the fuzzy reasoning of present invention described above, which correspond to the voxel of "tumor" shown in FIG. 9A. It can be the that the higher intensity corresponds to the higher grade.

More specifically, FIG. 9A is a cross sectional image of malignant tumor in a zx-plane in a voxel data. (size; 128×128×128 voxel). Midst of the image can be seen a cancer region (malignant tumor) and the surroundings are the normal tissues.

Figure 9B:
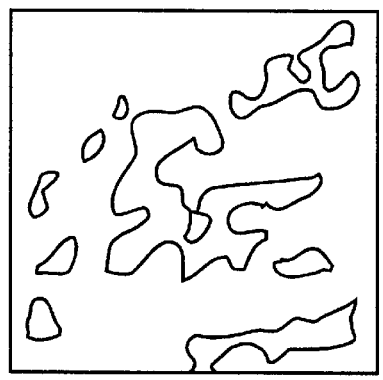

FIG. 9B shows the output of 3D-Gaussian-Laplace filter in case of σ=5, corresponds to the malignant tumor shown in FIG. 9A. Tumor region can be seen as darker area, normal tissue as gray and zero crossing area as white in the image. According to this example shown in FIG. 9B, even in the "tumor" region, not tumor region, but low intensity region in reality, is often exists. Therefore, "tumor" region invades "normal tissue" area (as in the obtained data).

Figure 9C:
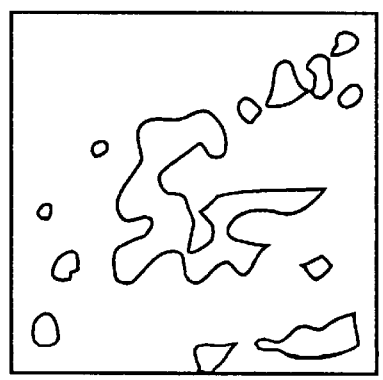

But, once applied the dilation and erosion process of present invention, erosion and small volume region which causes defects in the image can be terminated as shown in FIG. 9C.

FIG. 17 shows a flow chart of procedure of the determination of "tumor", "normal tissue" and "boundary" by relaxation method, i.e., fuzzy reasoning process and defuzzifying process for determining or diagnosing tumors.

The defuzzifying process having a labeling process labeling of all the voxels correspond to maximum grade amongst image($\mu_t$) which shows "tumor" grade, image($\mu_n$) which shows "normal tissue" grade or image($\mu_b$) which shows "boundary" grade(S1), and having label number calculating process(S2–S5) letting $N_t$, $N_n$, $N_b$ be the number of voxel in the 3×3×3 voxel volume, which is counted by the voxel having the largest value among $\{\mu_t, \mu_n, \mu_b\}$ and parallel iterating process applying local constraints to the numbers in iterations(S6–S9, and back to S2);

The local constraints are expressed as follows:

R1: if $N_t \geq 1$ and $N_b \geq 2$ and $N_n \geq 1$ then $\mu_t\text{--}, \mu_n\text{--}, \mu_b\text{++}$ R2: else if $N_n = 0$ and $N_b \geq 1$ and $N_t \geq 1$ then $\mu_t\text{++}, \mu_n\text{--}, \mu_b\text{--}$ R3: else if $N_t = 0$ and $N_b \geq 1$ and $N_n \geq 1$ then $\mu_t\text{--}, \mu_n\text{++} \mu_b\text{--}$ R4: else if $N_t > N_n + 12$ then $\mu_t\text{++}, \mu_n\text{--}, \mu_b\text{--}$ R5: else if $N_n > N_t + 12$ then $\mu_t\text{--}, \mu_n\text{++}, \mu_b\text{--}$ R6: else then $\mu_t\text{--}, \mu_n\text{--}, \mu_b\text{++}$ where, the sign of "++" means that a constant C will be added to the corresponding grade, and the sign of "--" means the grade is decreased by C.

And it must be noted that constant=12 at R4 and R5 means difference between $N_n$, $N_t$ in 3×3×3 region connected with a voxel of interest is rather big. This constant is of experimental. The inventors of present invention have been studied to determining the constant as a most favorable for most effective defuzzification by trying a series of experiments. And the consequence is that C=0.25. But when the value gets over 1.0, then C=1.0, or when the value gets lower than 0.0, then C=0.0.

The labeling process includes rendering process renewing values of the grades of "tumor" grade, "normal tissue" grade and "boundary" grade.

This defuzzifying process is carried out in parallel and in iterations, and it lasts until the differential of the sum of $\mu_t$, $\mu_n$, $\mu_b$ gets down under a predetermined threshold(S9-S11).

But, in some clinical case, closed tumor region surrounded by "normal tissues" in ROI(Region of Interest) includes misclassifyed normal tissue region(voxels corresponds to normal tissue; actually, that is not a tumor region).

In this kind of case, real tumor region is determined according to the rules described as follows:
1. On the assumption that whole data of voxel of interest is surrounded by "normal tissues", start with the normal tissues"to find a tumor voxel.
2. Finding all the voxels connected to the voxel that is already found in the "normal tissues". And to label the voxel as tumor 1.

3. The rule 2. Is carried out in iterations to label the voxels as tumor 1, tumor 2, tumor 3 . . . tumor n.
4. Arrange the labeled tumor k (k=1,2,3 . . . n) in order, dispose the voxels smaller than 2 mm in size. This size is defined as a radius of imaginary sphere represents the voxel. And among the rest of the tumors, determining a voxel that has a nearest center of gravity to the ROI (Region Of intensity), while other "tumors"(in voxel datum) are disposed.

For example, even a grade pb of the boundary of a voxel is large before execute the process, if the voxel is surrounded by tumors or normal tissues, the grade is to be changed down to the smaller value. And the grade $\mu_t, \mu_n$ is to be changed down to the larger value. Contrary to this, even the grade $\mu_b$ of the boundary of a voxel is large before carrying out this process, if there are more than two boundary graded voxels and/or more than one tumor graded voxels and/or more than one normal tissue graded voxels, the grade is to be changed (down) to the smaller value.

And the grade $\mu_t, \mu_n$ is to be changed to the larger value if the voxel is surrounded by tumors or normal tissues, the grade $\mu_b$ is to be changed (up) to the smaller larger value, and the grade $\mu_t, \mu_n$ is to be changed (down) to the smaller value.

The index calculating process is a process for evaluating morphological roughness of tumor as the object, wherein having normalizing process for normalizing the k to set the parameter(r)=1 when the object's surface is spherical.

Figure 18A:
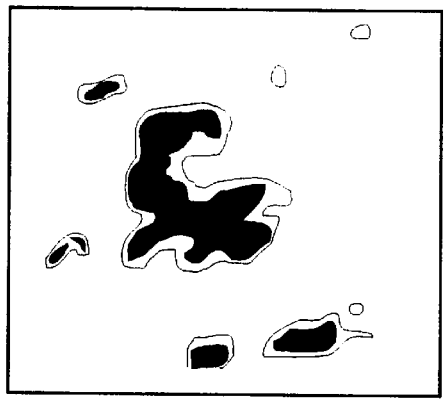
FIGS. 18A–18C show 3D-image of morphological surface extracted from a tumor.

FIG. 18A shows 3D-image of morphological surface extracted from a tumor by employing the defuzzifying process. And more specifically, FIG. 18A shows the image of zx-plane in voxel data superimposed, and a computer rendered 3D-image of the extracted tumor.

The higher intensity region corresponds to the boundary, lower region corresponds to the tumor, and intermediate intensity region corresponds to normal tissue.

Figure 18B:
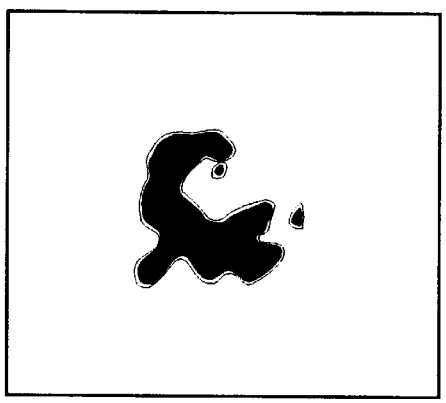

FIG. 18B shows the boundaries of the extracted benign tumor.

Figure 18C:
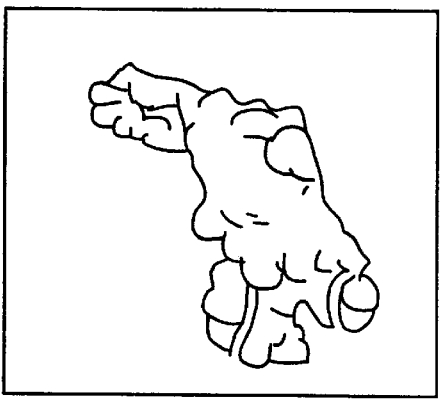

FIG. 18C shows an extracted 3D-image of morphological surface of the tumor.

The 3D-image is obtained by applying Lambert-shading method to each voxels in 5×5×5 cubic near to the extracted boundary.

It can be observed that morphological surface roughness is rendered clearly.

The calculating process calculating volume of the finally decided tumor's voxels as sum of the voxels;

And, further comprises tumor surface space calculating process which includes a process for making a set of neighboring three voxels all of which labeled as the outline of the tumor, and a process for calculating a sum of value of space in a triangle made of the three voxels.

Malignant Tumor Auto Discriminating Process

The malignant tumor auto discriminating process is for discriminating a degree of surface roughness of a tumor based on the voxel data.

Figure 19:
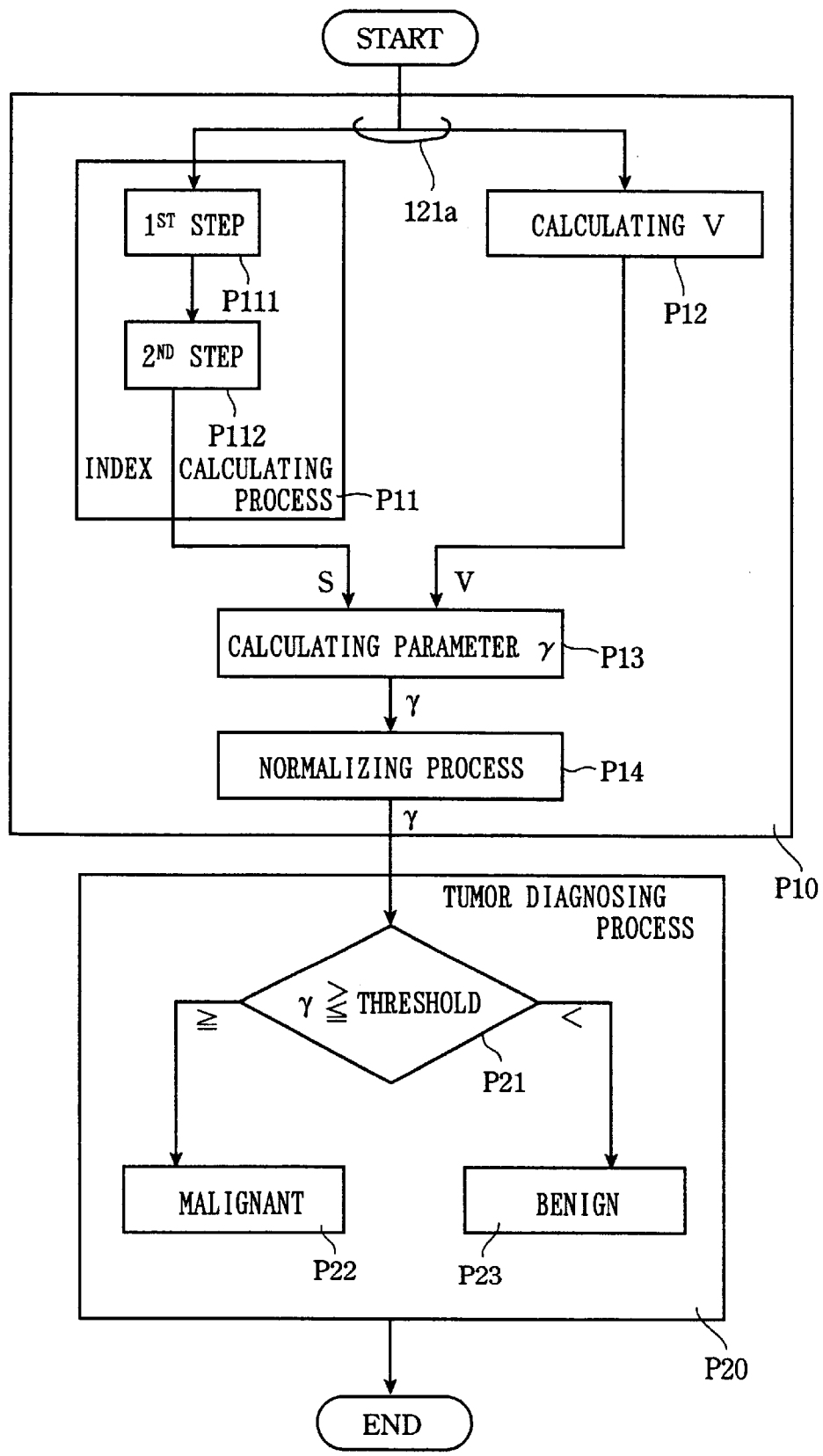
FIG. 19 is a flow of malignant tumor auto determining process.
Figure 22A:
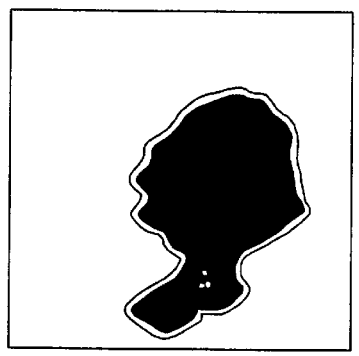
FIGS. 22A and 22B show the boundaries of the extracted benign tumor and the image of zx-plane in voxel data superimposed, and a computer rendered 3D-image of the extracted tumor in case no.4, respectively.
Figure 22B:
Figure 23A:
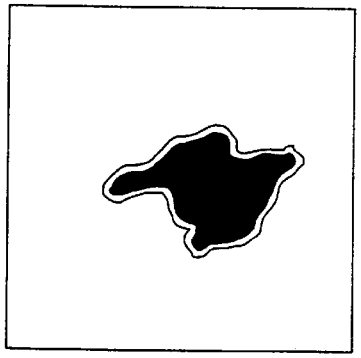
FIGS. 23A and 23B show the boundaries of the extracted benign tumor, and the image of zx-plane in voxel data superimposed, and a computer rendered 3D-image of the extracted tumor(b) in case no.6, respectively.
Figure 23B:
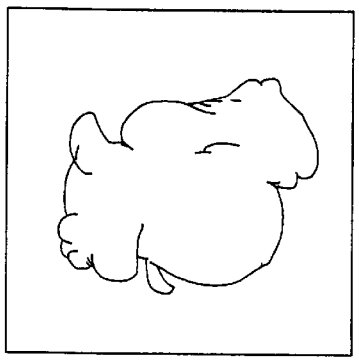
Figure 24A:
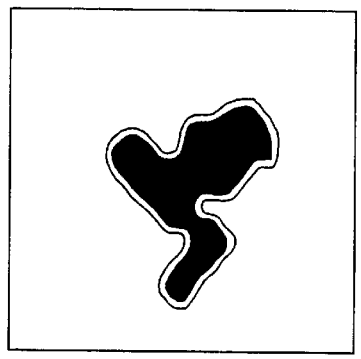
FIGS. 24A and 24B show the boundaries of the extracted benign tumor and the image of zx-plane in voxel data superimposed, and a computer rendered 3D-image of the extracted tumor in case no.8, respectively.
Figure 24B:
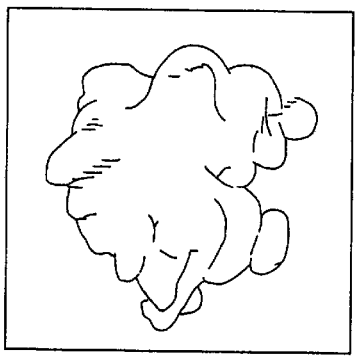
Figure 25A:
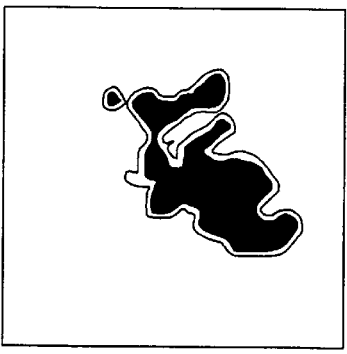
FIGS. 25A and 25B show the boundaries of the extracted benign tumor and the image of zx-plane in voxel data superimposed, and a computer rendered 3D-image of the extracted tumor in case no.10, respectively.
Figure 25B:
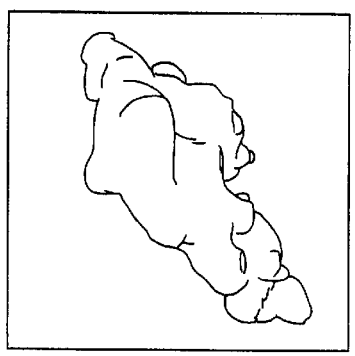
Figure 26A:
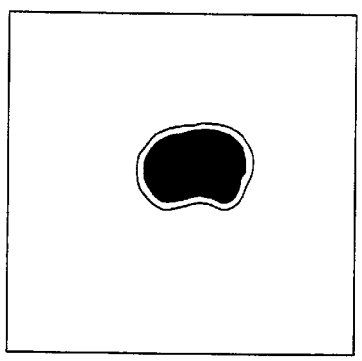
FIGS. 26A and 26B show the boundaries of the extracted benign tumor and the image of zx-plane in voxel data superimposed, and a computer rendered 3D-image of the extracted tumor in case no.19, respectively.
Figure 26B:
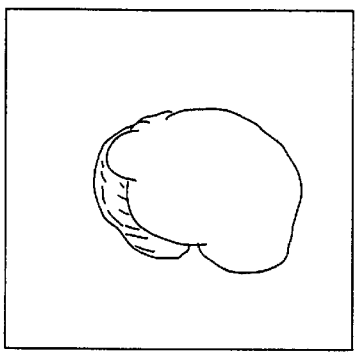
Figure 27A:
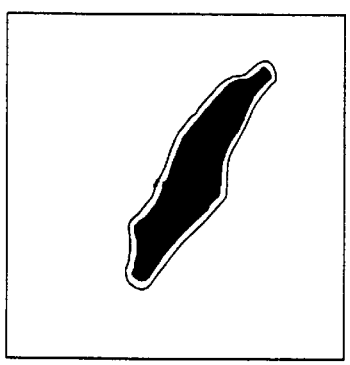
FIGS. 27A and 27B show the boundaries of the extracted benign tumor and the image of zx-plane in voxel data superimposed, and a computer rendered 3D-image of the extracted tumor in case no.20, respectively.
Figure 27B:
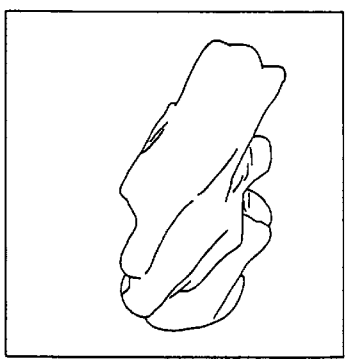
Figure 28A:
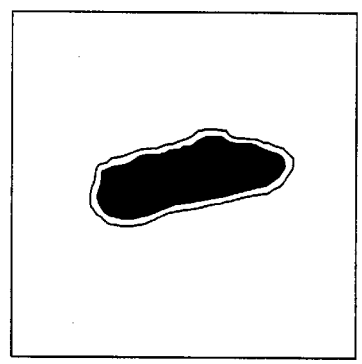
FIGS. 28A and 28B show the boundaries of the extracted benign tumor and the image of zx-plane in voxel data superimposed, and a computer rendered 3D-image of the extracted tumor in case no.25, respectively.
Figure 28B:
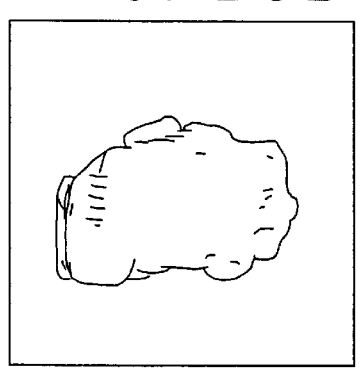
Figure 29A:
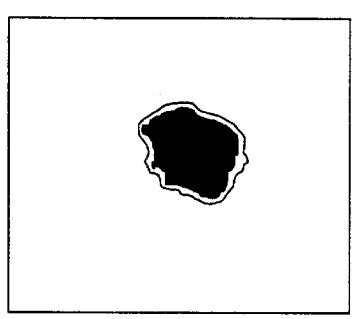
FIGS. 29A and 29B show the boundaries of the extracted benign tumor and the image of zx-plane in voxel data superimposed, and a computer rendered 3D-image of the extracted tumor in case no.26, respectively.
Figure 29B:
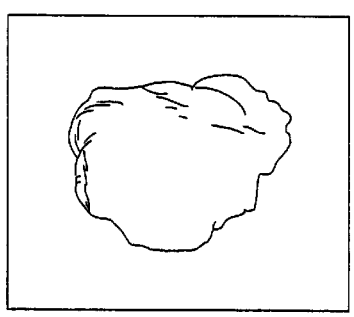
Figure 32:
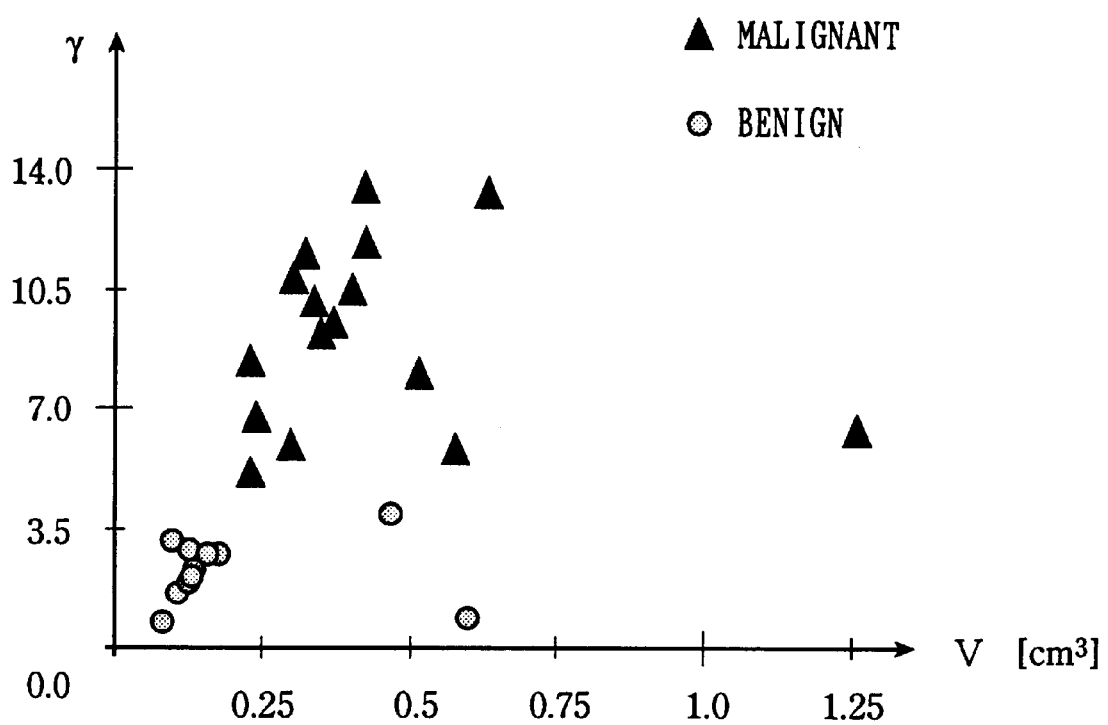
FIG. 32 shows the relation of the parameter r (or S/V ratio) and the volume of the extracted tumors.

And wherein the process further comprises:

Morphological surface roughness calculating process for calculating parameter (r) using a surface area (S) and a volume (V) of the object as an index of degree of uneven complexity of the surface roughness. The value V is calculated in P12 (shown in FIG. 19), and S is calculated in P11 (wherein, the $1^{st}$ process P111, the $2^{nd}$ process P112 are included).

The process also comprises Figure judging process (S13) for judging the morphological surface as smooth when the (r) is less than predetermined threshold, or as rough when the (r) is the threshold (S/V ratio. In this embodiment, the ratio S/V≈4 as the threshold) or more, while the parameter (r) defined as r=$(S^3/V^2)/\kappa, \kappa$=constant.

And also comprises tumor diagnosing process for judging the tumor as malignant tumor when the judgement is "rough", or judging the tumor as benign tumor when the judgement is "smooth"(P20). More specifically, when r is larger than the threshold (S21), the tumor is judged as "malignant" (P21~P22), or r is smaller than the threshold (S21), the tumor is judged as "benign" (S23).

FIG. 20 shows the examples of tumor diagnosis carried out with the system of present invention in the clinical practice. The result is that the system used this embodiment of present invention diagnose 16 cases as malignant tumor and 11 cases as benign tumor. These conclusions are shown at the column in FIG. 20. And wherein the tumors are 0.5~1.8 in size.

FIGS. 21A~30A (in each FIGS.) shows the examples of tumor diagnosis carried out with the system of present invention in the clinical practice.

The tumor regions are extracted and rendered quite clearly in FIGS. 21B~30B (in each FIGS.) shows the image of zx-plane in voxel data superimposed, and a computer rendered 3D-image of the extracted tumor. According to the superimposed image, the tumor regions are extracted and rendered quite clearly. And also it can be observed that the cancer region is spreading and penetrating into the surrounding areas.

In FIGS. 21B~25B, morphological roughness, the most significant feature of the malignant tumor such as "cancer", can be clearly recognized.

On the other hand, In FIGS. 26B~30B, smooth surface, the most significant feature of the benign tumor is shown clearly. Therefore, the inspector can carry out quite reliable diagnosis with the method and apparatus of present invention. And it must be noted that even an inspector who does not yet enough experience can achieve a quite reliable extraction and diagnosis of the tumor only with scanning the probe and watching the 3D-image correspond to the tumor region As described above, extraction of breast tumors from three-dimensional ultrasonic images can be realized by interpolation of a series of cross sectional images. And in the second stage, the membership function is used for a fuzzy logic based calculation or operation to produce three grades of the voxel attributable to three classes of "tumor", "normal tissue", and "boundary" effectively with high reliability. Then classifying each voxel as one of the three classes by relaxation techniques. Also, a parameter for evaluation of the uneven complexity of the surface roughness using a ratio of the surface area over the volume is defined.

As shown in FIGS. 20–30 and described above, The results show that both of the two types of extracted tumors agree well with the manually traced boundaries, and the evaluation parameter also perform a distinct difference between the two types of tumors.

Now, over viewing again the tumor diagnosis system in which the methods and means of the present invention described above.

Methods in this embodiment of the present invention has:
3D-image obtaining process
Tumor extracting process
Malignant tumor auto determining process.

More specifically, the 3D-image obtaining process includes:
Probe process S1
3D-position sensor process S2
Tracking process
3D-coordinates converting process S3
3D-voxel data generating process S4.

More specifically, tumor extracting process includes:
Index operating process;
Membership function auto generating process;
Fuzzy reasoning process;
Defuzzifying process.

Malignant tumor auto determining process more specifically includes:
Morphological surface roughness calculating process;
Figure judging process;
Tumor diagnosing process.

Each of the processes can be carried out by means that has the same name as the means perform therewith. For example, 3D-voxel data generating method executes the 3D-voxel data generating process S4, and so one . . . .

More specifically, in this embodiment, 3D-image obtaining process is carried out by Aloca Co, SSD-2000 (ultrasonic diagnosis mean) 20, probe mean 12(with ultrasonic probe 121), and 3D-position sense mean(with alternate magnetic field sensor 131)

3D-image obtaining process, tracking process, 3D-position sensor process S2, 3D-coordinate convert process, and a part of 3D-voxel data generating process S4 are carried out by the 3D-space system (Polhemus Co. Fastrack) 14.

3D-coordinates converting process S3 is carried out by the Frame Grabber(Data Translation Co. DT3155), and a part of the 3D-voxel data generating process S4, the tumor extracting process, the malignant tumor auto discriminating process.

Although it must be noted that the arrangement such as which process should be done in which part of the system can be changed according to the system configuration and/or OS data format etc . However, it must be noted that the programs for carrying out the diagnosis methods (or the diagnosis system) of the present invention can be installed even in a PC described above because those programs are of smaller quantities. And the programs for carrying out the diagnosis methods (or the diagnosis system) of the present invention performs quite well in extracting and diagnosing tumors in clinical case because it employs the fuzzy reasoning and defuzzifying method as described above.

What is claimed is:

1. Method for tumor extraction comprising the process of:
process for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
process for generating membership function includes process for extracting automatically said tumor region by arranging said arithmetic volume distribution according to fuzzy reasoning which employs said membership function;
process for fuzzy reasoning for classifying said each voxels into predetermined plural of types of region according to said generated membership function and fuzzy rules thereof;
process for carrying out defuzzify process to said each voxels according to a relaxation technique.

2. Method for tumor extraction comprising the process of:
process for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
process for generating membership function includes process for extracting automatically said tumor region by arranging said arithmetic volume distribution according to fuzzy reasoning which employs said membership function;
fuzzy reasoning process for classifying said each voxels into predetermined plural of types of region according to said generated membership function and fuzzy rules thereof;
process for carrying out defuzzify process to said each voxels according to a relaxation technique, followed by;
defuzzifying process for finally determining tumor region by classifying "tumor", "normal tissue" or "boundary";
and said fuzzy reasoning process includes a process to determine a likeness of said voxel as "tumor", "normal tissue" or "boundary" and to classify said voxel corresponding to said degree.

3. Method for tumor extraction comprising the steps of:
process for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
process for generating membership function includes process for extracting automatically said tumor region by arranging said arithmetic volume distribution according to fuzzy reasoning which employs said membership function;
process for fuzzy reasoning for classifying said each voxels into predetermined plural of types of region according to said generated membership function and fuzzy rules thereof;
process for carrying out defuzzify process to said each voxels according to a relaxation technique;
process for defuzzifying and finally determining tumor region by classifying said voxel "tumor", "normal tissue" or "boundary";

said arithmetic volume includes an average value of intensity;

said intensity=$\{\ddagger\ddagger\ddagger f(I,j,k)\}/N^3$, while, I,j,k=0,1,2, . . . N−1 (N=natural number), and said f(I,j,k) represents a value of intensity of voxel volume and $\ddagger$ is a mathematical symbol.

4. Apparatus for tumor extraction comprising the means of:

- means for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
- means for generating membership function includes means for extracting automatically said tumor region by arranging said arithmetic volume distribution according to fuzzy reasoning which employs said membership function;
- means for fuzzy reasoning for classifying said each voxels into predetermined plural of types of region according to said generated membership function and fuzzy rules thereof;
- means for carrying out defuzzify means to said each voxels according to a relaxation technique.

5. Apparatus for tumor extraction comprising the means of:

- means for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
- means for generating membership function includes means for extracting automatically said tumor region by arranging said arithmetic volume distribution according to fuzzy reasoning which employs said membership function;
- fuzzy reasoning means for classifying said each voxels into predetermined plural of types of region according to said generated membership function and fuzzy rules thereof;
- means for carrying out defuzzify means to said each voxels according to a relaxation technique, followed by;
- defuzzifying means for finally determining tumor region by classifying "tumor", "normal tissue" or "boundary";
- and said fuzzy reasoning means includes a means to determine a likeness of said voxel as "tumor", "normal tissue" or "boundary" and to classify said voxel corresponding to said degree.

6. Apparatus for tumor extraction comprising the means of:

- means for operating index of uneven complexity of the surface roughness which expresses arithmetic volume distribution which concerning tumor regions, normal tissues and tumor boundary between said tumor regions and normal tissues on a ultrasonic echographic image of each three dimensional voxels as probability distribution in [0,1] region of membership function which is employed a fuzzy reasoning;
- means for generating membership function includes means for extracting automatically said tumor region by arranging said arithmetic volume distribution according to fuzzy reasoning which employs said membership function;
- means for fuzzy reasoning for classifying said each voxels into predetermined plural of types of region according to said generated membership function and fuzzy rules thereof;
- means for carrying out defuzzify means to said each voxels according to a relaxation technique;
- means for defuzzifying and finally determining tumor region by classifying said voxel "tumor", "normal tissue" or "boundary";
- said arithmetic volume includes an average value of intensity;
- said intensity=$\{\ddagger\ddagger\ddagger f(I,j,k)\}/N^3$, while, I,j,k=0,1,2, . . . N−1 (N=natural number), and said f(I,j,k) represents a value of intensity of voxel volume and $\ddagger$ is a mathematical symbol.

* * * * *